US010851421B2

(12) United States Patent
Lai et al.

(10) Patent No.: US 10,851,421 B2
(45) Date of Patent: Dec. 1, 2020

(54) NEXT GENERATION RNA-SEQUENCING AND LONG NON-CODING RNA IN GLIOBLASTOMA MULTIFORME

(71) Applicant: University of Southern California, Los Angeles, CA (US)

(72) Inventors: Rose Lai, San Ramon, CA (US); Chao Ling, Beijing (CN); Darryl Nousome, La Palma, CA (US); Kai Wang, Agoura Hills, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 0 days.

(21) Appl. No.: 15/456,285

(22) Filed: Mar. 10, 2017

(65) Prior Publication Data

US 2017/0260592 A1      Sep. 14, 2017

Related U.S. Application Data

(60) Provisional application No. 62/307,235, filed on Mar. 11, 2016.

(51) Int. Cl.
*C12Q 1/68* (2018.01)
*C12Q 1/6886* (2018.01)
*C12N 15/113* (2010.01)

(52) U.S. Cl.
CPC .......... *C12Q 1/6886* (2013.01); *C12N 15/113* (2013.01); *C12N 2310/113* (2013.01); *C12N 2310/14* (2013.01); *C12N 2310/20* (2017.05); *C12Q 2600/118* (2013.01); *C12Q 2600/158* (2013.01); *C12Q 2600/178* (2013.01)

(58) Field of Classification Search
None
See application file for complete search history.

(56) References Cited

PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Bady et al., MGMT methylation analysis of glioblastoma on the Infinium methylation BeadChip identifies two distinct CpG regions associated with gene silencing and outcome, yielding a prediction model for comparisons across datasets, tumor grades, and CIMP-status, Acta neuropathologica, 2012, vol. 124, pp. 547-560.
Chen et al., Differential IncRNA expression profiles in recurrent gliomas compared with primary gliomas identified by microarray analysis, Int J Clin Exp Med, 2015, vol. 8, pp. 5033-5043.
Chu et al., Technologies to probe functions and mechanisms of longnoncoding RNAs, Nat Struct Mol Biol, 2015, vol. 22, abstract only.
Diaz-Beya et al., The lincRNA HOTAIRM1 located in the HOXA genomic region, is expressed in acute myeloid leukemia, impacts prognosis in patients in the intermediate-risk cytogenetic category, and is associated with a distinctive microRNA signature, Oncotarget, 2015, vol. 6, pp. 31613-31627.
Gupta et al., Long non-coding RNA HOTAIR reprograms chromatin state to promote cancer metastasis, Nature, 2010, vol. 464, pp. 1071-1076.
Han et al., LncRNA pro fi le of glioblastoma reveals the potential role of lncRNAs in contributing to glioblastoma pathogenesis. Int J Oncol, 2012, vol. 40, pp. 2004-2012.
Iyer et al., The landscape of long noncoding RNAs in the human transcriptome, Nat Genet, 2015, vol. 47, pp. 199-208.
Sati et al., Genome-wide analysis reveals distinct patterns of epigenetic features in long non-coding RNA loci, Nucleic acids research, 2012, vol. 40, pp. 10018-10031.
Su et al., Comprehensive analysis of long non-coding RNAs in human breast cancer clinical subtypes, Oncotarget, 2014, vol. 5, pp. 9864-9876.
Webb et al., RNA sequencing of transcriptomes in human brain regions: protein-coding and non-coding RNAs, isoforms and alleles, BMC Genomics, 2015, vol. 16, pp. 1-16.
Zhang et al., A myelopoiesis-associated regulatory intergenic noncoding RNA transcript within the human HOXA cluster, Blood, 2009, vol. 113, pp. 2526-2534.
Zhang et al., Long non-coding RNA Expression profiles predict clinical phenotypes in glioma, Neurobiol Dis, 2012, vol. 48, abstract only.
Zhang et al., A long non-coding RNA signature in glioblastoma multiforme predicts survival, Neurobiol Dis, 2013, vol. 58, abstract only.
Zhang et al., Long non-coding RNA HOTAIR promotes glioblastoma cell cycle progression in an EZH2 dependent manner, Oncotarget, 2015, vol. 6, pp. 537-546.

* cited by examiner

*Primary Examiner* — James Martinell
(74) *Attorney, Agent, or Firm* — Nixon Peabody LLP

(57) ABSTRACT

LncRNAs are emerging as important oncogenic drivers in many cancers, but comprehensive, agnostic studies to identify key lncRNAs involved in GBM are lacking. Described herein are new lncRNA involved in gliomagenesis and prognosis, elucidating the biological functions of these relatively unknown biological actors and opening new therapeutic avenues for therapeutic development.

10 Claims, 8 Drawing Sheets

Specification includes a Sequence Listing.

SEQUENCE LISTING

<160> NUMBER OF SEQ ID NOS: 56

<210> SEQ ID NO 1
<211> LENGTH: 23
<212> TYPE: DNA
<213> ORGANISM: Artificial Sequence
<220> FEATURE:
<223> OTHER INFORMATION: HOX-AS2-f

<400> SEQUENCE: 1
tccccctgaa agtaaatgtc ctt                                         23

<210> SEQ ID NO 2
<211> LENGTH: 20
<212> TYPE: DNA
<213> ORGANISM: Artificial Sequence
<220> FEATURE:
<223> OTHER INFORMATION: HOX-AS2-r

<400> SEQUENCE: 2
cccgtgtttg ctgaatcctt                                             20

<210> SEQ ID NO 3
<211> LENGTH: 21
<212> TYPE: DNA
<213> ORGANISM: Artificial Sequence
<220> FEATURE:
<223> OTHER INFORMATION: RP11-745C15.2-f

<400> SEQUENCE: 3
ttttggagca caagccttct g                                           21

<210> SEQ ID NO 4
<211> LENGTH: 18
<212> TYPE: DNA
<213> ORGANISM: Artificial Sequence
<220> FEATURE:
<223> OTHER INFORMATION: RP11-745C15.2-r

<400> SEQUENCE: 4
cacgacgatg ccatggaa                                               18

<210> SEQ ID NO 5
<211> LENGTH: 20

```
<212> TYPE: DNA
<213> ORGANISM: Artificial Sequence
<220> FEATURE:
<223> OTHER INFORMATION: H19-f

<400> SEQUENCE: 5
tcccagaacc cacaacatga                                              20

<210> SEQ ID NO 6
<211> LENGTH: 20
<212> TYPE: DNA
<213> ORGANISM: Artificial Sequence
<220> FEATURE:
<223> OTHER INFORMATION: H19-r

<400> SEQUENCE: 6
gggttttgtg tccggattca                                              20

<210> SEQ ID NO 7
<211> LENGTH: 20
<212> TYPE: DNA
<213> ORGANISM: Artificial Sequence
<220> FEATURE:
<223> OTHER INFORMATION: RP11-545H22.1-f

<400> SEQUENCE: 7
cctctggaca tgccatgaaa                                              20

<210> SEQ ID NO 8
<211> LENGTH: 25
<212> TYPE: DNA
<213> ORGANISM: Artificial Sequence
<220> FEATURE:
<223> OTHER INFORMATION: RP11-545H22.1-r

<400> SEQUENCE: 8
tcctatctct ccttggtctt caaaa                                        25

<210> SEQ ID NO 9
<211> LENGTH: 19
<212> TYPE: DNA
<213> ORGANISM: Artificial Sequence
<220> FEATURE:
<223> OTHER INFORMATION: LUCAT1-f

<400> SEQUENCE: 9
ccaacgcttg ccaaatcct                                               19

<210> SEQ ID NO 10
<211> LENGTH: 24
<212> TYPE: DNA
<213> ORGANISM: Artificial Sequence
<220> FEATURE:
<223> OTHER INFORMATION: LUCAT1-r

<400> SEQUENCE: 10
acggtagtga cagcatcaaa actc                                         24

<210> SEQ ID NO 11
<211> LENGTH: 20
<212> TYPE: DNA
<213> ORGANISM: Artificial Sequence
<220> FEATURE:
<223> OTHER INFORMATION: RP11-731F5.2-f

<400> SEQUENCE: 11
```

```
ggccgagctg tgatttccta                                              20
```

<210> SEQ ID NO 12
<211> LENGTH: 20
<212> TYPE: DNA
<213> ORGANISM: Artificial Sequence
<220> FEATURE:
<223> OTHER INFORMATION: RP11-731F5.2-r

<400> SEQUENCE: 12

```
gggtctcagc ccttcctgtt                                              20
```

<210> SEQ ID NO 13
<211> LENGTH: 24
<212> TYPE: DNA
<213> ORGANISM: Artificial Sequence
<220> FEATURE:
<223> OTHER INFORMATION: RP11-439H9.1-f

<400> SEQUENCE: 13

```
tttgtaccac cctaaccttt gctt                                         24
```

<210> SEQ ID NO 14
<211> LENGTH: 21
<212> TYPE: DNA
<213> ORGANISM: Artificial Sequence
<220> FEATURE:
<223> OTHER INFORMATION: RP11-439H9.1-r

<400> SEQUENCE: 14

```
ctgcttaaca tgctgcaacc a                                            21
```

<210> SEQ ID NO 15
<211> LENGTH: 20
<212> TYPE: DNA
<213> ORGANISM: Artificial Sequence
<220> FEATURE:
<223> OTHER INFORMATION: RP11-84A19.3-f

<400> SEQUENCE: 15

```
ggaccctgct gtgtctggaa                                              20
```

<210> SEQ ID NO 16
<211> LENGTH: 18
<212> TYPE: DNA
<213> ORGANISM: Artificial Sequence
<220> FEATURE:
<223> OTHER INFORMATION: RP11-84A19.3-r

<400> SEQUENCE: 16

```
gcaggccttt gggctctt                                                18
```

<210> SEQ ID NO 17
<211> LENGTH: 22
<212> TYPE: DNA
<213> ORGANISM: Artificial Sequence
<220> FEATURE:
<223> OTHER INFORMATION: RP1-170O19.23-f

<400> SEQUENCE: 17

```
gcaccaggaa agaggacaat tc                                           22
```

<210> SEQ ID NO 18
<211> LENGTH: 18
<212> TYPE: DNA
<213> ORGANISM: Artificial Sequence

```
<220> FEATURE:
<223> OTHER INFORMATION: RP1-170O19.23-r

<400> SEQUENCE: 18
cggtggctcc cagaagct                                                 18

<210> SEQ ID NO 19
<211> LENGTH: 20
<212> TYPE: DNA
<213> ORGANISM: Artificial Sequence
<220> FEATURE:
<223> OTHER INFORMATION: HOXA-AS3-f

<400> SEQUENCE: 19
gctgcatcca agggtaaacc                                               20

<210> SEQ ID NO 20
<211> LENGTH: 20
<212> TYPE: DNA
<213> ORGANISM: Artificial Sequence
<220> FEATURE:
<223> OTHER INFORMATION: HOXA-AS3-r

<400> SEQUENCE: 20
gcaaagcact ccatgacgaa                                               20

<210> SEQ ID NO 21
<211> LENGTH: 18
<212> TYPE: DNA
<213> ORGANISM: Artificial Sequence
<220> FEATURE:
<223> OTHER INFORMATION: RP1-140K8.5-f

<400> SEQUENCE: 21
acagggtccc ccgacaga                                                 18

<210> SEQ ID NO 22
<211> LENGTH: 20
<212> TYPE: DNA
<213> ORGANISM: Artificial Sequence
<220> FEATURE:
<223> OTHER INFORMATION: RP1-140K8.5-r

<400> SEQUENCE: 22
agcacgaact gtccccagat                                               20

<210> SEQ ID NO 23
<211> LENGTH: 17
<212> TYPE: DNA
<213> ORGANISM: Artificial Sequence
<220> FEATURE:
<223> OTHER INFORMATION: AC096579.7-f

<400> SEQUENCE: 23
ttcggccaag ggaccaa                                                  17

<210> SEQ ID NO 24
<211> LENGTH: 20
<212> TYPE: DNA
<213> ORGANISM: Artificial Sequence
<220> FEATURE:
<223> OTHER INFORMATION: AC096579.7-r

<400> SEQUENCE: 24
gatggcggga agatgaagac                                               20
```

```
<210> SEQ ID NO 25
<211> LENGTH: 18
<212> TYPE: DNA
<213> ORGANISM: Artificial Sequence
<220> FEATURE:
<223> OTHER INFORMATION: HOXA-AS4-f

<400> SEQUENCE: 25
tgggaggctc aggatgga                                                 18

<210> SEQ ID NO 26
<211> LENGTH: 22
<212> TYPE: DNA
<213> ORGANISM: Artificial Sequence
<220> FEATURE:
<223> OTHER INFORMATION: HOXA-AS4-r

<400> SEQUENCE: 26
gtggtaggaa ttctgggctt tg                                            22

<210> SEQ ID NO 27
<211> LENGTH: 22
<212> TYPE: DNA
<213> ORGANISM: Artificial Sequence
<220> FEATURE:
<223> OTHER INFORMATION: RP11-1151B14.4-f

<400> SEQUENCE: 27
tggctttctc tgctatcagc aa                                            22

<210> SEQ ID NO 28
<211> LENGTH: 20
<212> TYPE: DNA
<213> ORGANISM: Artificial Sequence
<220> FEATURE:
<223> OTHER INFORMATION: RP11-1151B14.4-r

<400> SEQUENCE: 28
gaattggccc cctctgaaat                                               20

<210> SEQ ID NO 29
<211> LENGTH: 18
<212> TYPE: DNA
<213> ORGANISM: Artificial Sequence
<220> FEATURE:
<223> OTHER INFORMATION: HOTAIRM1-f

<400> SEQUENCE: 29
ggcttccgca gtgatgga                                                 18

<210> SEQ ID NO 30
<211> LENGTH: 19
<212> TYPE: DNA
<213> ORGANISM: Artificial Sequence
<220> FEATURE:
<223> OTHER INFORMATION: HOTAIRM1-r

<400> SEQUENCE: 30
cgactgcgcg tcacctaga                                                19

<210> SEQ ID NO 31
<211> LENGTH: 22
<212> TYPE: DNA
<213> ORGANISM: Artificial Sequence
<220> FEATURE:
<223> OTHER INFORMATION: GNAS-AS1-f
```

<400> SEQUENCE: 31
cccaggatgg ataaggagtt ga                                              22

<210> SEQ ID NO 32
<211> LENGTH: 23
<212> TYPE: DNA
<213> ORGANISM: Artificial Sequence
<220> FEATURE:
<223> OTHER INFORMATION: GNAS-AS1-r

<400> SEQUENCE: 32
ctggtagcca gtcacttcca ctt                                             23

<210> SEQ ID NO 33
<211> LENGTH: 17
<212> TYPE: DNA
<213> ORGANISM: Artificial Sequence
<220> FEATURE:
<223> OTHER INFORMATION: HOXA-AS2-f

<400> SEQUENCE: 33
cgggcccttt gcgtcta                                                    17

<210> SEQ ID NO 34
<211> LENGTH: 24
<212> TYPE: DNA
<213> ORGANISM: Artificial Sequence
<220> FEATURE:
<223> OTHER INFORMATION: HOXA-AS2-r

<400> SEQUENCE: 34
aagaggttac ctgggtctga gtga                                            24

<210> SEQ ID NO 35
<211> LENGTH: 25
<212> TYPE: DNA
<213> ORGANISM: Artificial Sequence
<220> FEATURE:
<223> OTHER INFORMATION: HOXB-AS3-f

<400> SEQUENCE: 35
tatagaaacc aggacgtccc ttagc                                           25

<210> SEQ ID NO 36
<211> LENGTH: 17
<212> TYPE: DNA
<213> ORGANISM: Artificial Sequence
<220> FEATURE:
<223> OTHER INFORMATION: HOXB-AS3-r

<400> SEQUENCE: 36
cgctggtgcg gatatcg                                                    17

<210> SEQ ID NO 37
<211> LENGTH: 21
<212> TYPE: DNA
<213> ORGANISM: Artificial Sequence
<220> FEATURE:
<223> OTHER INFORMATION: RP11-366L20.3-f

<400> SEQUENCE: 37
ggttacatgg gagggtttgg t                                               21

<210> SEQ ID NO 38

```
<211> LENGTH: 22
<212> TYPE: DNA
<213> ORGANISM: Artificial Sequence
<220> FEATURE:
<223> OTHER INFORMATION: RP11-366L20.3-r

<400> SEQUENCE: 38
agaaggtgca gagcagcaag tt                                              22

<210> SEQ ID NO 39
<211> LENGTH: 25
<212> TYPE: DNA
<213> ORGANISM: Artificial Sequence
<220> FEATURE:
<223> OTHER INFORMATION: RP1-58B11.1-f

<400> SEQUENCE: 39
gccagaagac atgtaaacag tgaca                                           25

<210> SEQ ID NO 40
<211> LENGTH: 25
<212> TYPE: DNA
<213> ORGANISM: Artificial Sequence
<220> FEATURE:
<223> OTHER INFORMATION: RP1-58B11.1-r

<400> SEQUENCE: 40
aggagtggag aagcattaca agatg                                           25

<210> SEQ ID NO 41
<211> LENGTH: 20
<212> TYPE: DNA
<213> ORGANISM: Artificial Sequence
<220> FEATURE:
<223> OTHER INFORMATION: SAA2-SAA4-f

<400> SEQUENCE: 41
tgacggcctg cctaagaaat                                                 20

<210> SEQ ID NO 42
<211> LENGTH: 19
<212> TYPE: DNA
<213> ORGANISM: Artificial Sequence
<220> FEATURE:
<223> OTHER INFORMATION: SAA2-SAA4-r

<400> SEQUENCE: 42
tgtggctcac agcccagtt                                                  19

<210> SEQ ID NO 43
<211> LENGTH: 22
<212> TYPE: DNA
<213> ORGANISM: Artificial Sequence
<220> FEATURE:
<223> OTHER INFORMATION: HOTAIR-f

<400> SEQUENCE: 43
cctagccttt ggaagctctt ga                                              22

<210> SEQ ID NO 44
<211> LENGTH: 22
<212> TYPE: DNA
<213> ORGANISM: Artificial Sequence
<220> FEATURE:
<223> OTHER INFORMATION: HOTAIR-r

<400> SEQUENCE: 44
```
tgtcttggag aggcgtgtaa ca                                    22

<210> SEQ ID NO 45
<211> LENGTH: 25
<212> TYPE: DNA
<213> ORGANISM: Artificial Sequence
<220> FEATURE:
<223> OTHER INFORMATION: RP11-79H23.3-f

<400> SEQUENCE: 45
agagagaagg catactgttg atggt                                 25

<210> SEQ ID NO 46
<211> LENGTH: 23
<212> TYPE: DNA
<213> ORGANISM: Artificial Sequence
<220> FEATURE:
<223> OTHER INFORMATION: RP11-79H23.3-r

<400> SEQUENCE: 46
cagcacgtga cttttgttgt ttt                                   23

<210> SEQ ID NO 47
<211> LENGTH: 23
<212> TYPE: DNA
<213> ORGANISM: Artificial Sequence
<220> FEATURE:
<223> OTHER INFORMATION: RP11-246K15.1-f

<400> SEQUENCE: 47
gaggcaaaca tgttccaaag aag                                   23

<210> SEQ ID NO 48
<211> LENGTH: 25
<212> TYPE: DNA
<213> ORGANISM: Artificial Sequence
<220> FEATURE:
<223> OTHER INFORMATION: RP11-246K15.1-r

<400> SEQUENCE: 48
gcattgtatc ttttcggtga atttt                                 25

<210> SEQ ID NO 49
<211> LENGTH: 22
<212> TYPE: DNA
<213> ORGANISM: Artificial Sequence
<220> FEATURE:
<223> OTHER INFORMATION: AC010729.1-f

<400> SEQUENCE: 49
tcagggacag gcttgaagat tc                                    22

<210> SEQ ID NO 50
<211> LENGTH: 17
<212> TYPE: DNA
<213> ORGANISM: Artificial Sequence
<220> FEATURE:
<223> OTHER INFORMATION: AC010729.1-r

<400> SEQUENCE: 50
tcctgccgag gctgaca                                          17

<210> SEQ ID NO 51
<211> LENGTH: 22
<212> TYPE: DNA

```
<213> ORGANISM: Artificial Sequence
<220> FEATURE:
<223> OTHER INFORMATION: hACTINalpha-f

<400> SEQUENCE: 51
caggaccgtg tggagcagat tg                                              22

<210> SEQ ID NO 52
<211> LENGTH: 22
<212> TYPE: DNA
<213> ORGANISM: Artificial Sequence
<220> FEATURE:
<223> OTHER INFORMATION: hACTINalpha-r

<400> SEQUENCE: 52
cagattgtcc cactggtcac ag                                              22

<210> SEQ ID NO 53
<211> LENGTH: 20
<212> TYPE: DNA
<213> ORGANISM: Artificial Sequence
<220> FEATURE:
<223> OTHER INFORMATION: hGAPDH-f

<400> SEQUENCE: 53
tgccctcaac gaccactttg                                                 20

<210> SEQ ID NO 54
<211> LENGTH: 23
<212> TYPE: DNA
<213> ORGANISM: Artificial Sequence
<220> FEATURE:
<223> OTHER INFORMATION: hGAPDH-r

<400> SEQUENCE: 54
ctcttcctct tgtgctcttg ctg                                             23

<210> SEQ ID NO 55
<211> LENGTH: 22
<212> TYPE: DNA
<213> ORGANISM: Artificial Sequence
<220> FEATURE:
<223> OTHER INFORMATION: hRPLP0-f

<400> SEQUENCE: 55
cgctatccgc ggtttctgat tg                                              22

<210> SEQ ID NO 56
<211> LENGTH: 23
<212> TYPE: DNA
<213> ORGANISM: Artificial Sequence
<220> FEATURE:
<223> OTHER INFORMATION: hRPLP0-r

<400> SEQUENCE: 56
aaagacgatg tcacttccac gag                                             23
```

NEXT GENERATION RNA-SEQUENCING AND LONG NON-CODING RNA IN GLIOBLASTOMA MULTIFORME

CROSS-REFERENCE TO RELATED APPLICATION

This application claims the benefit of U.S. Provisional Application No. 62/307,235, filed Mar. 11, 2016.

STATEMENT REGARDING FEDERALLY SPONSORED RESEARCH OR DEVELOPMENT

This invention was made with government support under Grant No. CA014089 awarded by the National Institutes of Health. The government has certain rights in the invention.

FIELD OF THE INVENTION

Described herein are methods and compositions related to long non-coding RNA (lncRNAs) and their role in brain diseases and conditions, such as glioblastoma.

BACKGROUND

Glioblastoma multiforme (GBM), also known as glioblastoma and grade IV astrocytoma, is the most common and aggressive cancer in the brain. The cause of most cases is unclear. They can either start from normal brain cells or develop from an already existing low-grade astrocytoma. The diagnosis is typically made by a combination of CT scan, MRI scan, and tissue biopsy. Glioblastomas represent 15% of brain tumors. Presently, there are no clear preventive measures against glioblastoma initiation, formation and development. Treatment typically involves surgery after which chemotherapy and radiation therapy is used. In some instances, the medication temozolomide is frequently used as part of chemotherapy.

In GBM, there has been extremely little research that has comprehensively identified significant long non-coding RNAs (lncRNAs). These sequences are an important class of pervasive genes involved in diverse biological functions and play key roles in oncogenesis. Well-characterized lncRNAs have functional roles in epigenetic transcriptional regulation, modulation of gene enhancers, inhibition of tumor suppressor activities, and regulation of mRNA processing and protein translation. Many lncRNA-based biomarkers and therapeutics are currently under clinical development.

In GBM, no studies have yet used next-generation sequencing to discover key lncRNA involved in this tumor's pathogenesis and prognosis. There are few validated biomarkers, and no biomarker-based targeted therapy exists for treatment of this deadly disease. The very small body of literature on lncRNA in GBM only used publicly available microarray datasets that contained very limited number of known lncRNAs. Thus, there is a great need in the art to identify lncRNAs that may play a key role in the initiation, formation, and development of GBM.

Described herein are methods and compositions relying on next-generation RNA-Sequencing technologies to discover differentially expressed lncRNA and to evaluate their prognostic values in overall survival of this disease. In the Inventors' differential expression study of 19 GBM and 20 control brains, 7 of the top 10 lncRNAs were within the 4 HOMEOBOX gene clusters. Five of these 7, including the top lncRNA HOXD-AS2 (named HOTAG1), were novel to GBM pathogenesis. In the prognosis study using 153 Cancer Genome Atlas' GBM samples, 8 previously unknown intergenic lncRNA were significant for overall survival. According to Ingenuity Pathway Analyses, the top lncRNA, RP3-449M8.9 (named SAGENT1) in 14q23.3 was strongly associated with transcriptional pathways of innate and acquired immunity. Overall 18 of the top 20 lncRNA in differential expression and 8 lncRNA significant for overall survival were new discovery that can serve the development of therapeutics or novel biomarkers for GBM. From these results, new prognostic biomarkers for this cancer and novel therapeutics based on the Inventors' findings are described.

SUMMARY OF THE INVENTION

Described herein is a method of prognosing susceptibility to a brain tumor including providing a sample from a subject and detecting one or more long non-coding RNAs (lncRNAs) in the sample, wherein the detected level of the one or more lncRNAs in the same from the subject compared to a reference level of the one or more lncRNAs prognoses susceptibility to a brain tumor. In other embodiments, the brain tumor includes glioblastoma multiforme (GBM). In other embodiments, the brain tumor includes astrocytoma. In other embodiments, the one or more lncRNAs includes HOXD-AS2 (HOTAG1), HOXA-AS2 (HOTAG2), HOXA-AS4 (HOTAG3), HOTAIR, RP11-366L20.3, AC069363.1, HOXA-AS3 (HOTAG4), HOXB-AS3 (HOTAG5), HOTAIRM1, RP11-290F20.3, DIAPH3-AS1, RP11-416O18.1, RP11-439H9.1, AC074011.2, RP11-742B18.1, RP11-246K15.1, AC005281.1, LUCAT1, RP11-412H8.2, and/or RP11-536K7.5. In other embodiments, detecting one or more long non-coding RNAs (lncRNAs) includes ribo-depleted RNA sequencing. In other embodiments, detecting one or more long non-coding RNAs (lncRNAs) includes quantitative real-time PCR (qRT-PCR).

Also described herein is a method of determining the presence or absence of a brain tumor including providing a sample from a subject and detecting one or more long non-coding RNAs (lncRNAs) in the sample, wherein the detected level of the one or more lncRNAs in the same from the subject compared to a reference level of the one or more lncRNAs determines the presence or absence of a brain tumor in the subject. In other embodiments, the brain tumor includes glioblastoma multiforme (GBM). In other embodiments, the brain tumor includes astrocytoma. In other embodiments, the one or more lncRNAs includes HOXD-AS2 (HOTAG1), HOXA-AS2 (HOTAG2), HOXA-AS4 (HOTAG3), HOTAIR, RP11-366L20.3, AC069363.1, HOXA-AS3 (HOTAG4), HOXB-AS3 (HOTAG5), HOTAIRM1, RP11-290F20.3, DIAPH3-AS1, RP11-416O18.1, RP11-439H9.1, AC074011.2, RP11-742B18.1, RP11-246K15.1, AC005281.1, LUCAT1, RP11-412H8.2, and/or RP11-536K7.5. In other embodiments, detecting one or more long non-coding RNAs (lncRNAs) includes ribo-depleted RNA sequencing. In other embodiments, detecting one or more long non-coding RNAs (lncRNAs) includes quantitative real-time PCR (qRT-PCR).

Further described herein is a method of treating a brain disease and/or condition including selecting a subject afflicted with a brain disease and/or condition, and administering a pharmaceutical composition to the subject, wherein the pharmaceutical composition is capable of treating the brain disease and/or condition, and wherein the brain disease and/or conditions includes the presence of a brain tumor in the subject. In other embodiments, the brain tumor includes glioblastoma multiforme (GBM). In other embodiments, the brain tumor includes astrocytoma. In other embodiments, the pharmaceutical composition is capable of modulating the expression of one or more lncRNAs including HOXD-AS2 (HOTAG1), HOXA-AS2 (HOTAG2), HOXA-AS4 (HOTAG3), HOTAIR, RP11-366L20.3, AC069363.1, HOXA-AS3 (HOTAG4), HOXB-AS3 (HOTAG5), HOTAIRM1, RP11-290F20.3, DIAPH3-AS1, RP11-416O18.1, RP11-439H9.1, AC074011.2, RP11-742B18.1, RP11-246K15.1, AC005281.1, LUCAT1, RP11-412H8.2, and/or RP11-536K7.5. In other embodiments, treating the brain disease and/or condition includes a reduction in brain tumor size. In other embodiments, treating the brain disease and/or condition includes retardation of brain tumor growth. In other embodiments, treating the brain disease and/or condition includes elimination of the brain tumor. In other embodiments, treating the brain disease and/or condition is adjuvant to standard therapy. In other embodiments, the pharmaceutical composition includes a protein, antibody and/or aptamer. In other embodiments, the pharmaceutical composition includes a small molecule. In other embodiments, the small molecule is capable of modifying epigenetic status. In other embodiments, the pharmaceutical composition includes a nucleic acid. In other embodiments, the nucleic acid includes an antisense nucleic acid and/or a small interfering RNA (siRNA).

BRIEF DESCRIPTION OF FIGURES

FIG. 3.

FIG. 5.

FIG. 6.

DETAILED DESCRIPTION

Figure 1:
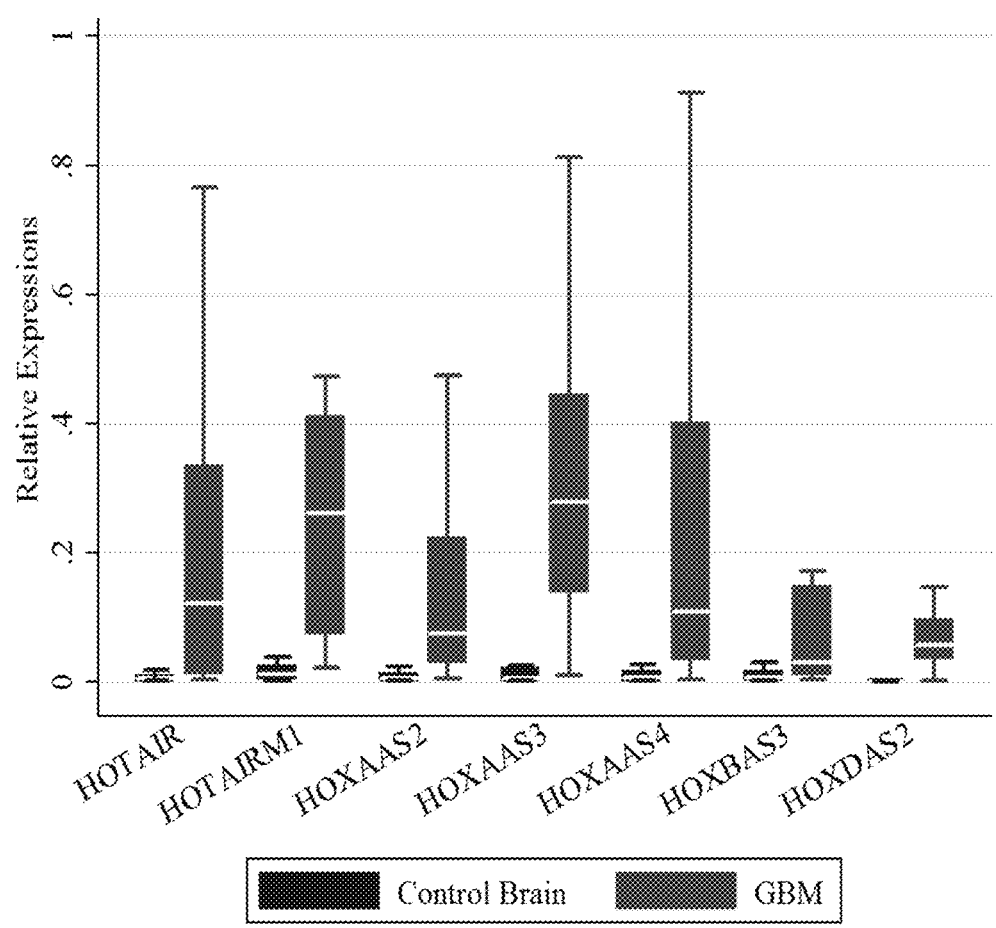
FIG. 1. Relative expressions of the 7 HOX gene cluster lncRNAs as measured by RT-PCR in GBM and control brains. Red bars denoted tumors, and blue bars represented control brains. Relative expression of each sample was calculated by the equation: relative expression= $2^{(average\ housekeeping\ genes\ Ct-target\ gene\ Ct)}$.

In glioblastoma multiforme (GBM), there has been a paucity of studies that comprehensively identified significant long non-coding RNAs (lncRNAs), which are now recognized to play key roles in oncogenesis. Therefore, the Inventors used next-generation RNA-Sequencing, ribo-depleted RNA-Seq, to discover differentially expressed lncRNA and to evaluate their prognostic values in the overall survival of this disease.

As described, long non-coding RNA (lncRNA) has emerged as an important class of pervasive genes involved in diverse biological functions. Well-characterized lncRNAs showed functional roles in epigenetic transcriptional regulation, modulation of gene enhancers, inhibition of tumor suppressor activities, and regulation of mRNA processing and protein translation. The majority of these lncRNA-based biomarkers and therapeutics are currently under clinical development.

In GBM, no studies have yet used next-generation sequencing to discover key lncRNA involved in this tumor's pathogenesis and prognosis. There has been a paucity of validated biomarkers, and no biomarker-based targeted therapy has been approved for treatment of this deadly disease. The very small body of literature on lncRNA in GBM only used publicly available microarray datasets that contained very limited number of known lncRNAs. One study leveraged a compendium of 7,256 RNA-Seq libraries and identified 58,648 lncRNA genes in 27 tissues and cancer types, which included a number of lncRNAs in GBM; however, the study did not have control brain tissues to investigate GBM specific differential expression and did not provide results on clinical outcome.

Described herein are characterizations of long non-coding RNA expression that are relevant to GBM pathogenesis and prognosis. To discover lncRNA involved in gliomagenesis, the Inventors retrieved fresh-frozen GBM tissues and control brain specimens to evaluate differentially expression using next-gen RNA-Seq. To identify significant lncRNA in the overall survival of GBM, the Inventors turned to Cancer Genome Atlas (TCGA)'s RNA-Seq and corresponding clinical data. Because different RNA-Seq analytic tools may produce somewhat different findings, the Inventors used two bioinformatics pipelines and only nominated those lncRNA that reached significance in both methods.

In the Inventors' differential expression study of 19 GBM and 20 control brains, 7 of the top 10 lncRNAs were within the 4 HOMEOBOX gene clusters. Five of these 7, including the top lncRNA HOXD-AS2 (named HOTAG1), were novel to GBM pathogenesis. In the prognosis study using 153 Cancer Genome Atlas' GBM samples, 8 previously unknown intergenic lncRNA were significant for overall survival. According to Ingenuity Pathway Analyses, the top lncRNA, RP3-449M8.9 (named SAGENT1) in 14q23.3 was strongly associated with transcriptional pathways of innate and acquired immunity. The Inventors' investigation showed that lncRNAs might have clinical and biological relevance in GBM.

Described herein is a method of prognosing susceptibility to a brain tumor including providing a sample from a subject and detecting one or more long non-coding RNAs (lncRNAs) in the sample, wherein the detected level of the one or more lncRNAs in the same from the subject compared to a reference level of the one or more lncRNAs prognoses susceptibility to a brain tumor. In other embodiments, the brain tumor includes glioblastoma multiforme (GBM). In other embodiments, the brain tumor includes astrocytoma. In other embodiments, the one or more lncRNAs are derived from a HOX gene cluster. In other embodiments, the one or more lncRNAs includes HOXD-AS2 (HOTAG1), HOXA-AS2 (HOTAG2), HOXA-AS4 (HOTAG3), HOTAIR, RP11-366L20.3, AC069363.1, HOXA-AS3 (HOTAG4), HOXB-AS3 (HOTAG5), HOTAIRM1, RP11-290F20.3, DIAPH3-AS1, RP11-416O18.1, RP11-439H9.1, AC074011.2, RP11-742B18.1, RP11-246K15.1, AC005281.1, LUCAT1, RP11-412H8.2, and/or RP11-536K7.5. In various embodiments, detecting the one or more lncRNAs includes use of one or more of SEQ ID NO: 1-56. In other embodiments, detecting one or more long non-coding RNAs (lncRNAs) includes ribo-depleted RNA sequencing. In other embodiments, detecting one or more long non-coding RNAs (lncRNAs) includes quantitative real-time PCR (qRT-PCR). In various embodiments, the reference level includes a level representative of a population of normal subjects without disease. For example, reference values can be obtained from a population of normal subjects in The Cancer Genome Atlas. In various embodiments, the one or more lncRNAs are expressed at a level 3, 4, 5, 6, 7, 8, 9 or more times greater than a reference level from a normal subject, or level representative of normal subjects without disease. In various embodiments, the prognosis include survival prediction of about 4, 5, 6, 7, 8, 9, 10, 11, 12, 13, 14, 15, 16, 17, 18, 19, 20, 21, 22, 23, 24, 25 months.

Also described herein is a method of determining the presence or absence of a brain tumor including providing a sample from a subject and detecting one or more long non-coding RNAs (lncRNAs) in the sample, wherein the detected level of the one or more lncRNAs in the same from the subject compared to a reference level of the one or more lncRNAs determines the presence or absence of a brain tumor in the subject. In other embodiments, the brain tumor includes glioblastoma multiforme (GBM). In other embodiments, the brain tumor includes astrocytoma. In other embodiments, the one or more lncRNAs are derived from a HOX gene cluster. In other embodiments, the one or more lncRNAs includes HOXD-AS2 (HOTAG1), HOXA-AS2 (HOTAG2), HOXA-AS4 (HOTAG3), HOTAIR, RP11-366L20.3, AC069363.1, HOXA-AS3 (HOTAG4), HOXB-AS3 (HOTAG5), HOTAIRM1, RP11-290F20.3, DIAPH3-AS1, RP11-416O18.1, RP11-439H9.1, AC074011.2, RP11-742B18.1, RP11-246K15.1, AC005281.1, LUCAT1, RP11-412H8.2, and/or RP11-536K7.5. In various embodiments, detecting the one or more lncRNAs includes use of one or more of SEQ ID NO: 1-56. In other embodiments, detecting one or more long non-coding RNAs (lncRNAs) includes ribo-depleted RNA sequencing. In other embodiments, detecting one or more long non-coding RNAs (lncRNAs) includes quantitative real-time PCR (qRT-PCR). In various embodiments, the reference level includes a level representative of a population of normal subjects without disease. For example, reference values can be obtained from a population of normal subjects in The Cancer Genome Atlas. In various embodiments, the one or more lncRNAs are expressed at a level 3, 4, 5, 6, 7, 8, 9 or more times greater than a reference level from a normal subject, or level representative of normal subjects without disease.

Further described herein is a method of treating a brain disease and/or condition including selecting a subject afflicted with a brain disease and/or condition, and administering a pharmaceutical composition to the subject, wherein the pharmaceutical composition is capable of treating the brain disease and/or condition, and wherein the brain disease and/or conditions includes the presence of a brain tumor in the subject. In other embodiments, the brain tumor includes glioblastoma multiforme (GBM). In other embodiments, the brain tumor includes astrocytoma. In other embodiments, the pharmaceutical composition is capable of modulating the expression of one or more lncRNAs including HOXD-AS2 (HOTAG1), HOXA-AS2 (HOTAG2), HOXA-AS4 (HOTAG3), HOTAIR, RP11-366L20.3, AC069363.1, HOXA-AS3 (HOTAG4), HOXB-AS3 (HOTAG5), HOTAIRM1, RP11-290F20.3, DIAPH3-AS1, RP11-416O18.1, RP11-439H9.1, AC074011.2, RP11-742B18.1, RP11-246K15.1, AC005281.1, LUCAT1, RP11-412H8.2, and/or RP11-536K7.5. In various embodiments, detecting the one or more lncRNAs includes use of one or more of SEQ ID NO: 1-56. In other embodiments, treating the brain disease and/or condition includes a reduction in brain tumor size. In other embodiments, treating the brain disease and/or condition includes retardation of brain tumor growth. In other embodiments, treating the brain disease and/or condition includes elimination of the brain tumor. In other embodiments, treating the brain disease and/or condition is adjuvant to standard therapy. In other embodiments, the pharmaceutical composition includes a protein, antibody and/or aptamer. In other embodiments, the pharmaceutical composition includes a small molecule. In other embodiments, the small molecule is capable of modifying epigenetic status. In other embodiments, the pharmaceutical composition includes a nucleic acid. In other embodiments, the nucleic acid includes an antisense nucleic acid and/or a small interfering RNA (siRNA).

Example 1

GBM, Control Brain Samples and Pathological Verification

The Inventors retrieved 19 fresh-frozen de novo adult GBM from the University of Southern California Brain Tumor Bank. For controls, the Inventors obtained 20 fresh-frozen post-mortem adult brain tissues from the University of Miami Brain Bank. These non-tumor controls were neuropathologically verified to be without any neurological diseases. Brain tissues were cut into 8 μm section, and all tumor samples were laser micro-dissected as previously described to ensure inclusion of only viable tumor cells. Approximately 2000-3000 GBM cells per sample were collected from 8 μm sections. Tumors and control subjects' demographic and pathological characteristics were summarized in Table 3.

Total RNA was extracted using RNeasy Kit (Qiagen) with DNase I digestion according to the manufacturer's instructions. RNA integrity was verified on an Agilent Bioanalyzer 2100 (Agilent Technologies, Palo Alto, Calif.). cDNA was synthesized from 2 μg of total RNA using Superscript III (Life Technologies Inc.) and random primers (Life Technologies Inc.).

Example 2

Library Preparation and Sequencing

RNA Sequencing libraries were constructed using a ribodepletion approach in order to query all lncRNAs. RIN values varied from 6 to 10 but with ribodepletion this is not a factor. In all cases, the starting amount for library construction was one microgram of total RNA. Ribodepletion was carried out using the RiboZero Gold kit according to manufacturer's instructions. The ribodepleted material was introduced into the TruSeq Total RNA Library Preparation kit at the Elute-Fragmentation-Priming stage. Libraries were constructed according to manufacturer's instructions except the final PCR amplification to generate libraries was carried out for 12 and not 15 cycles. Library PCRs were cleaned with magnetic beads (AmpureXP, Beckman Coulter Genomics) and product visualized on an Agilent Bioanalyzer. Libraries were quantified by qPCR (Illumina library quantification kit, Kapa Biosystems) then run on an Illumina HiSeq 2000 as 50 cycles paired end reads with three samples pooled in each lane.

Example 3

Bioinformatics Analyses of Differential Expression Study

The Inventors performed quality control (QC) on the FASTQ files using FastQC. The Inventors did not observe adaptor contamination, and the Inventors' data passed all other QC measures. The FASTQ files were aligned to GENCODE v19 using TopHat-2.0.8. The mapping rate was over 95%. The aligned reads were processed using HT-Seq (version 0.6.0) to convert reads to gene counts. The Inventors used the R package DESeq2 (version 1.8.2) to perform variance stabilization of the data. The Inventors excluded genes with maximum counts <10 counts, and extreme values were truncated to the median expression value plus three times the interquartile range per gene. Afterward, the Inventors used DESeq2 for differential expression analyses between the 19 GBM and 20 brain controls. $Log_2$ fold change, and Q values (corrected for multiple testing) of each lncRNA were reported, and a twotailed Q value <0.05 was considered statistically significant.

To ensure the robustness of the Inventors' analyses, the Inventors also used the alternative RNA-Seq analytic pipeline Cuffdiff2 (version 2.1.1) for FPKM (Fragments Per Kilobase of transcript per Million mapped reads) calling and differential expression analyses. The Inventors excluded lncRNA with <10 FPKM and truncated extreme FPKM values to median plus three times the interquartile range. The final list of lncRNAs considered as differentially expressed was the set of long non-coding transcripts that overlapped between the 2 RNA-Seq analytic methods and reached FDR adjusted Q values of ≤0.05 in both analyses. Further analyses using this set of lncRNA were based on DESeq2.

Unsupervised Hierarchical Clustering was performed using Partek Genome Suite, and the top 10% of the highest standard deviation (SD) of lncRNA with Spearman ranked correlation were used for clustering. Database of lncRNAdb v2.0 and HGNG (http://www.genenames.org/cgibin/statistics) were used for further functional lncRNA re-annotation.

To evaluate the potential functions of top differentially expressed lncRNAs, the Inventors associated expressions of each significant lncRNA with mRNA genome-wide using Spearman rank correlation (FDR Q value ≤0.05). The list of significantly regulated mRNAs was functionally annotated using Ingenuity Pathway Analyses.

Example 4

Validation of Top Differentially Expressed lncRNA by RT-PCR

The 7 HOX gene clusters lncRNA and 18 other randomly chosen lncRNA within the top 20th percentile in $log_2$ fold changes (in both RNA-Seq methods) were subjected to RT-PCR validation. RNA samples from the same GBM and control brain subjects were quantitated by spectrophotometry and subsequently, 1 μg total RNA was used as template to synthesize cDNA with the High Capacity cDNA Reverse Transcription Kit (Applied Biosystems, Foster City, Calif.; Cat. no. 4368814). Primers for all assays were designed using Primer 3 (Table 8). Melting curve analysis was performed to insure single-product amplification for all primer pairs.

Real time PCR was performed on the ABI 7900HT Fast Real Time PCR System (Applied Biosystems) using these 25 lncRNA. Each reaction well contained 5 μL Power SYBR Green™ Master Mix (Applied Biosystems, Cat. no. 4367659), cDNA equivalent to 10 ng of total RNA and 150 nM each of forward and reverse amplification primers in a reaction volume of 10 μL.

Cycling conditions were as follows: 95° C. for 10 minutes for polymerase activation, followed by 40 cycles of 95° C. for 15 seconds and 60° C. for 1 minute. Data analysis was performed using Sequence Detection System software from Applied Biosystems, version 2.4. The experimental Ct (cycle threshold) was calibrated against the endogenous control products α Actin (ACTN1), Ribosomal protein, large, P0 (RPLP0) and Glyceraldehyde 3-phosphate dehydrogenase (GAPDH). Samples were analyzed for relative gene expression by the Ct method.

Example 5

TCGA RNA-Seq, Clinical, Genetic and Epigenetic Data

As most prognostic study of overall survival required substantial number of subjects, the Inventors turned to TCGA GBM datasets for their RNA-Seq and clinical data. Approval for use of Level 1 RNASeq and clinical information was granted by TCGA via dbGAP. 153 de novo GBM RNA-Seq FASTQ files were downloaded from Cancer Genomics Hub portal. Each sample was sequenced to an average of 60 million reads, with pair-ended read length of 75 bp generated on Illumina's Hi-Seq 2000 platform. All RNA-Seq data were generated using de novo GBM tissues obtained at initial diagnoses. Corresponding subjects' clinical data were retrieved from TCGA data portal; they included date of birth, date of diagnoses, gender, ethnicity, center, batch, treatment with concomitant radiotherapy and temozolomide (XRT/TMZ), duration of XRT/TMZ, use of Bevacizumab at recurrence, date of last follow-up, date of death and vital status. Pathological diagnoses of de novo GBM were verified with these subjects' pathology reports. MGMT methylation was determined using cg 12434587 and cg 12981137 on the Illumina methylation platforms. Isocitrate dehydrogenase 1 and 2 (IDH1 and 2) mutations and G-CIMP status were obtained from somatic mutation caller and level 3 methylation data, respectively.

Example 6

Bioinformatics and Statistical Analyses of Overall Survival Study

All FASTQ files passed quality controls using FASTQC. Similar to the Inventors' differential expression study, reads were aligned onto GENCODE 19 using TopHat-2.0.8. The Inventors used both the DESeq2 (version 1.8.2) and Cufflink2 (version 2.2.1) RNA-Seq pipelines to discover lncRNA transcripts for downstream prognostic evaluations. Data transformation and filtering for DESeq2 analyses were as previously described under the sub-section Bioinformatics analyses for differential expression study. Afterward, the Inventors normalized the raw counts between samples using DESeq2 normalization. For the Cufflink analyses, data transformation and filtering were also the same as the differential expression study. Cufflink was used to assemble transcriptomes of individual samples. Subsequently, the script Cuffmerge within Cufflink was used to merge assemblies, and Cuffnorm, which is a program within Cufflink, was employed to normalize transcripts across all libraries (via geometric means). The data were further $\log_2$ transformed before further analyses.

Following RNA-Seq analyses, Cox Proportional Hazard regressions were used to determine the impact of each lncRNA on the overall survival of GBM, adjusted by those covariates that were significant in univariable analyses. Cox regressions were performed separately for lncRNA quantified by DESeq2 and Cufflink2. False discovery rates were controlled using FDR Q value, with significance set at ≤0.05. Proportional hazard assumptions were verified using Schoenfeld residuals. The final list of prognostic lncRNAs was the set of FDR adjusted, significant long non-coding transcripts that overlapped between Cox modeling results derived from transcripts quantified by the two RNA-Seq methods. Further analyses using this set of lncRNA were based on DESeq2.

To perform internal model validations, TCGA RNA-Seq samples were randomly and equally divided into training and validation sets. The Inventors assessed model fit by comparing $R^2$ in the training and validation sets. 95% confidence intervals of $R^2$ were obtained via boot trapping with 5000 repetitions.

Example 7

Differential Expression Study

The demographic and pathological features of GBM and control subjects were summarized in Table 3. After quality control and filtering, DESeq2 and Cuffdiff2 identified 13,861 and 8,031 differentially expressed long non-coding transcripts, respectively. A total of 1742 lncRNAs were significant in both RNA-Seq methods after FDR adjustments (FDR Q value ≤0.05). Among these 1742 long non-coding transcripts, 826 were upregulated and 917 were downregulated. Table 4 listed the $\log_2$ fold changes, P values and FDR adjusted Q values for this set of significant lncRNAs analyzed with both pipelines. Table 1 showed the top 20 most differentially expressed lncRNAs ranked by the absolute values of the $\log_2$ fold changes based on DESeq2 results. All top 20 of them were upregulated in GBM. Of note, 7 of the top 10 were anti-sense or intergenic lncRNAs among the 4 HOMEOBOX (HOX) gene clusters, including the top differentially expressed lncRNA HOXD-AS2 (Table 1), which the Inventors named as HOTAG1 for HOX Transcript Associated with Glioblastoma 1. The others HOX gene clusters associated lncRNAs were HOTAIR, HOTAIRM1, HOXA-AS3, HOSA-AS4, HOXA-AS2 and HOXB-AS3. Moreover, consistent with DESeq2 findings, Cuffdiff2 found the 7 HOX related lncRNAs among the top 25 most differentially expressed long non-coding transcripts, with HOTAG1 also being the top most differentially expressed ($\log_2$ fold change=8.48, P=5.00 $E^{-05}$, Q=4.62 $E^{-04}$). Except HOTAIRM1 and HOTAIR, the other top lncRNAs were novel to GBM pathogenesis. RT-PCR was able to validate differential expressions of all 7 HOX gene clusters related lncRNAs and 17 randomly selected lncRNA within the top $20^{th}$ percentile (by $\log_2$ fold changes). Thus, 24 of the 25 lncRNA, with the exception of RP11-439H9.1, were found to be significant on differential expression by RT-PCR (Table 5). The relative expressions of the 7 HOX gene clusters related lncRNAs among GBM and control brains by RTPCR were shown in FIG. 1.

LncRNA expressions were then evaluated with respect to the 4 TCGA GBM gene expression classes using unsupervised hierarchical clustering. The pro-neural group had uniformly low expressions when compared to other expression groups and brain controls (FIG. 1). The expression patterns between mesenchymal and classical groups were indistinguishable. Only one GBM was classified as the neural group, and its lncRNA expression pattern was clustered together with normal cerebral cortex controls.

Similar to the results from hierarchical clustering, the expression of the top lncRNA, HOTAG1, was lowest in the pro-neural cluster, whereas its expression was the highest within the classical group (FIG. 1). HOTAG1 is located in 2q31.1 and is transcribed anti-sense to HOXD8 and HOXD9. Of note, among co-expressed mRNAs, it was most significantly and positively correlated with HOXD8 ($\beta$=1.06, P=8.11$E^{-34}$, Q=1.05$E^{-32}$), HOXD9 ($\beta$=0.96, P=2.45$E^{-21}$, Q=1.59$E^{-20}$) and HOXD10 ($\beta$=0.98, P=2.14$E^{-17}$, Q=9.26$E^{-17}$). Across the genome, it was coexpressed significantly with 771 mRNAs (Q<0.05). Ingenuity Pathway Analysis (IPA) based on these significantly correlated mRNAs showed the top pathway, Eukaryotic Initiation Factor-2 EIF2 (Q value=1.59 $E^{-29}$), is related to initiation of protein translation.

As shown in Table 9, the Inventors were able to further validate the top 20 differentially expressed lncRNA using TCGA's 4 normal brain samples and 153 de novo GBM samples. The RNA-seq processing and analytic pipelines were as described. These results further confirmed validation of of 19 of the 20 top differentially expressed lncRNA using the TCGA datasets, with only DIAPH3-AS1 failing to be validated in this additional secondary data set.

Example 8

Overall Survival Study

The demographic, clinical and pathological characteristics of the 153 GBM subjects with RNASeq data from TCGA. The median survival of this cohort was 13.34 months (interquartile range (IQR) 5.75-21.29 months). Clinical and molecular factors that were independent prognostic factors included: age at diagnoses (HR 1.02, 95% CI 1.01, 1.04, p=0.001)), MGMT methylation (cg12981137, HR 0.47, 95% CI 0.25-0.98, p=0.046), Glioma CpG Island Methylator Phenotype (GCIMP) status (HR 0.28, 95% CI 0.10, 0.79, p=0.016) and concomitant Temozolomide with radiotherapy (HR 0.42, 95% CI 0.28, 0.63, p=0.0001). Although IDH1 mutation was also an independent prognostic factor (HR 0.24, 95% CI 0.074-0.75, p=0.015), the Inventors only adjusted for GCIMP in subsequent multivariable Cox modeling due to strong correlation between IDH1 mutation and GCIMP (Spearman rho=0.84, p<0.00001). All lncRNA survival analyses were adjusted by these factors. After quality control and filtering, DESeq2 and Cufflink2 found 8,947 and 6,198 long non-coding transcripts, respectively. Multivariable Cox regression modeling discovered 8 lncRNA that were statistically significant for overall survival using both RNA-Seq methods and after FDR adjustments (Table 2, based on DESeq2 transcript assembly). Table 6 illustrated similar survival results of these 8 lncRNA using the alternative RNA-Seq method Cufflink2. Of note, both RNASeq pipelines led to the discovery of RP3-449M8.9 as the top most prognostic lncRNA in multivariable Cox modeling. Of the 8 long non-coding transcripts, 7 of them showed overexpressions were associated with poor survival. The exception was RP11-329B9.4, of which high expression was associated with favorable outcome (Table 2). In all Cox models, test of proportional hazard assumption using Schoenfeld Residuals did not demonstrate violation of proportional hazard assumptions. Assessment of model fit using $R^2$ did not find any differences in $R^2$ between training and validation data sets, as 0 were included in all 95% CI (Table 7).

Figure 2:
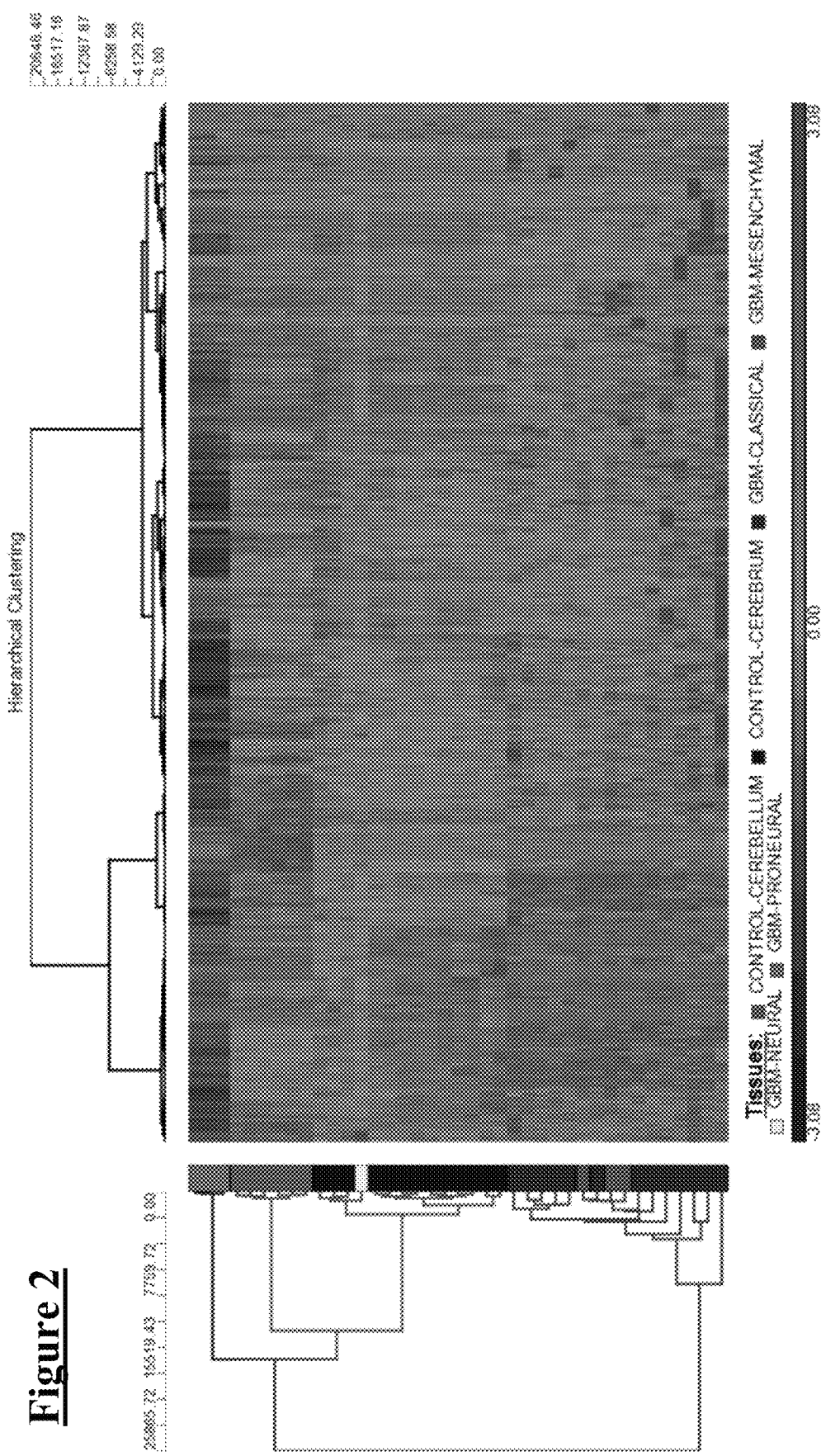
FIG. 2. Unsupervised hierarchical clustering of the top 10% of the highest standard deviation of lncRNA and their relationship with TCGA gene expression classes. Columns represented lncRNAs, and rows were control brain tissues or GBM tissues classified using TCGA gene expression clusters. Blue color denoted low expressions of lncRNA, whereas red characterized high levels of expressions.
Figure 3A:
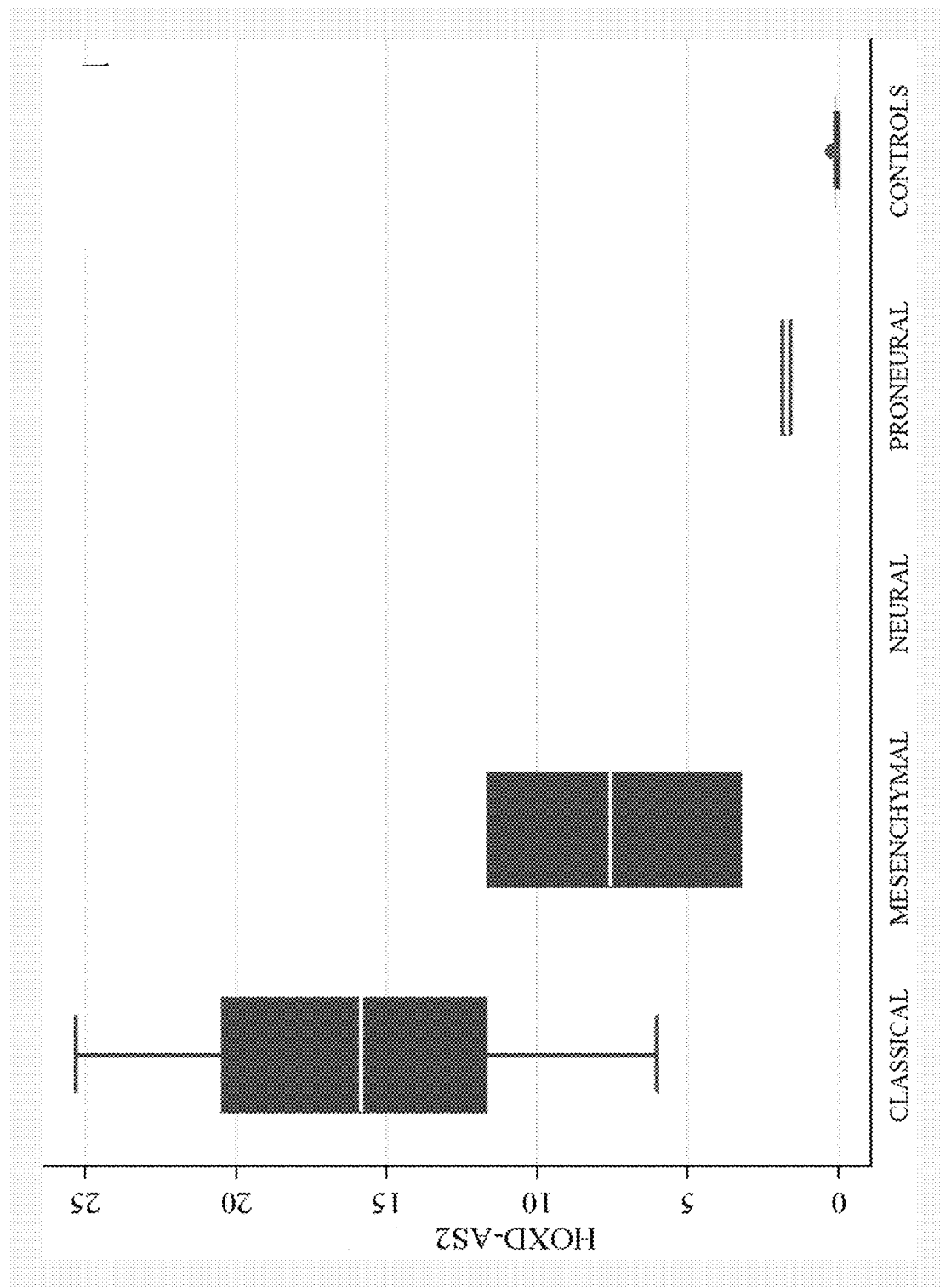
(FIG. 3A) Expression levels as measured by RNA-Seq of HOXD-AS2 (HOTAG1) in counts among the 4 TCGA gene expression classes and control brains.
Figure 3B:
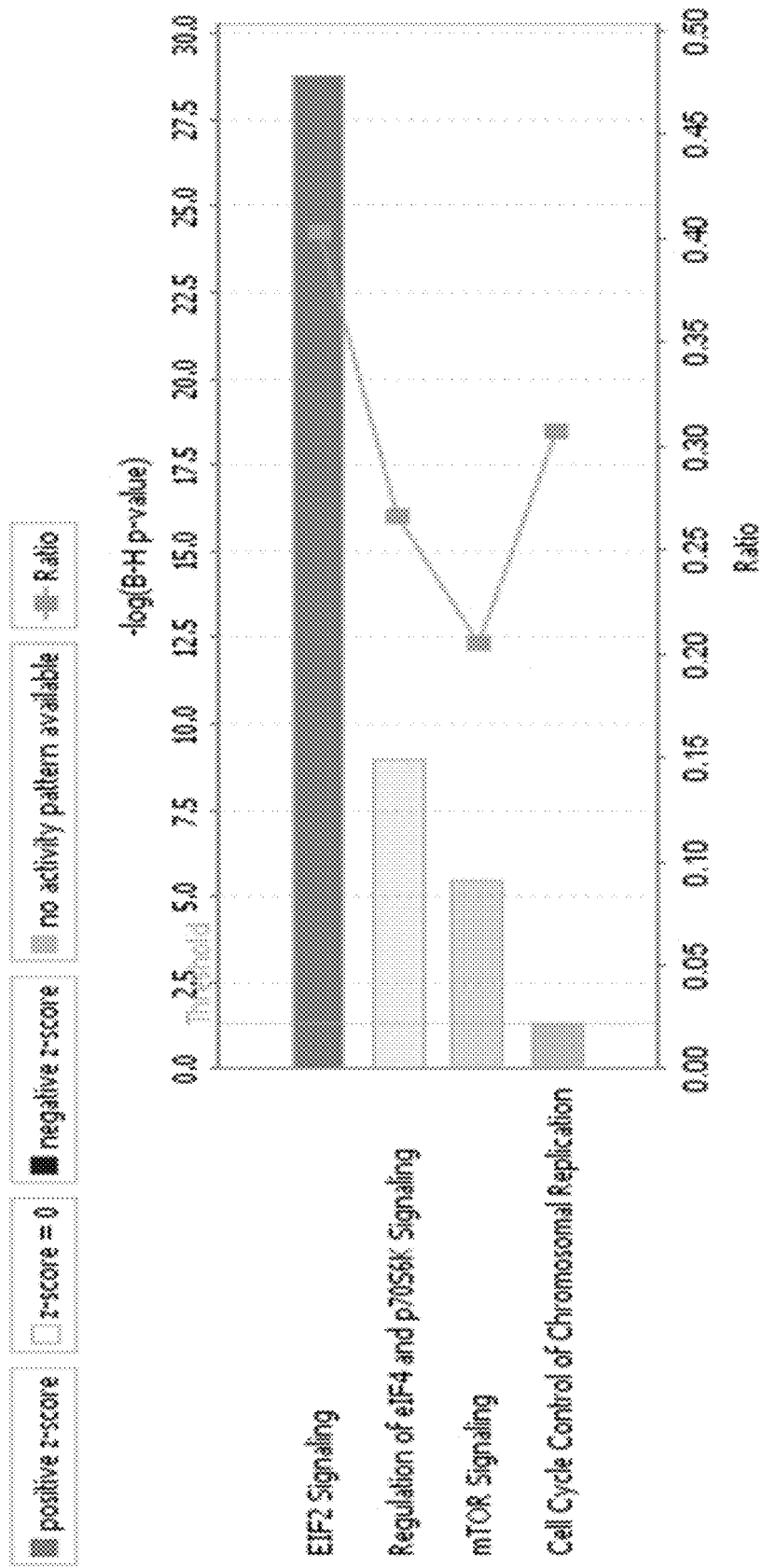
(FIG. 3B) IPA analyses of canonical pathways represented by significantly co-expressed mRNA of HOTAG1. The orange square denotes the ratio of number of genes presented in our dataset over the total number of genes in that pathway. The top horizontal axis represents FDR (Benjamin-Hochberg) corrected P value, and the bottom one denotes ratio of number of genes presented in the dataset over the total number of genes. The vertical dotted line (in orange) represents the threshold of statistical significance.
Figure 4:
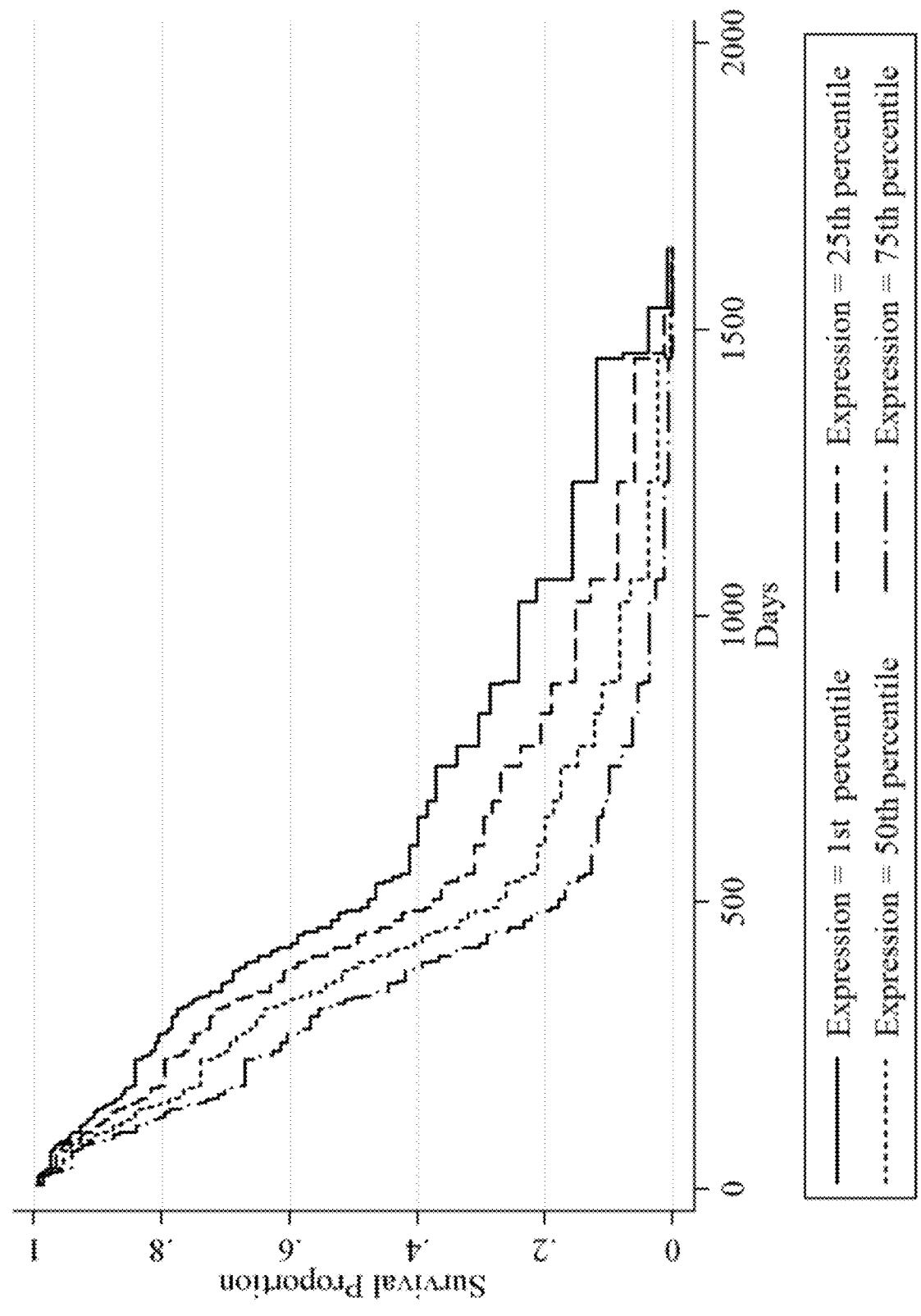
FIG. 4. Cox proportional hazard survival curves of RP3-449M8.9 (SAGENT1) expressions at the $1^{st}$, $25^{th}$, $50^{th}$ and $75^{th}$ percentiles, with all covariates held at median values.
Figure 5A:
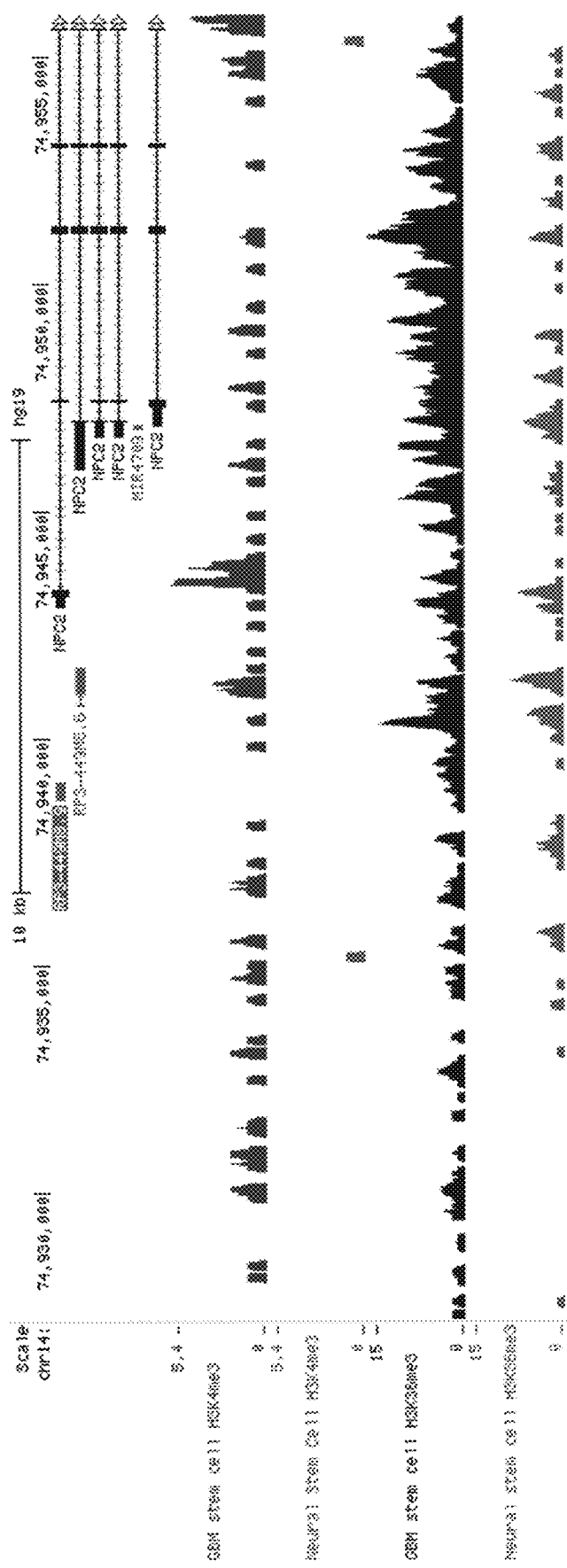
(FIG. 5A) ChIP-Seq data of H3K4me3 and H3K36me3 around SAGENT1 in the 14q24.3 regions, as shown in the UCSC Genome Browser. For each histone mark, ChIP-Seq data from GBM stem cells and non-neoplastic neural stem cells were displayed.
Figure 5B:
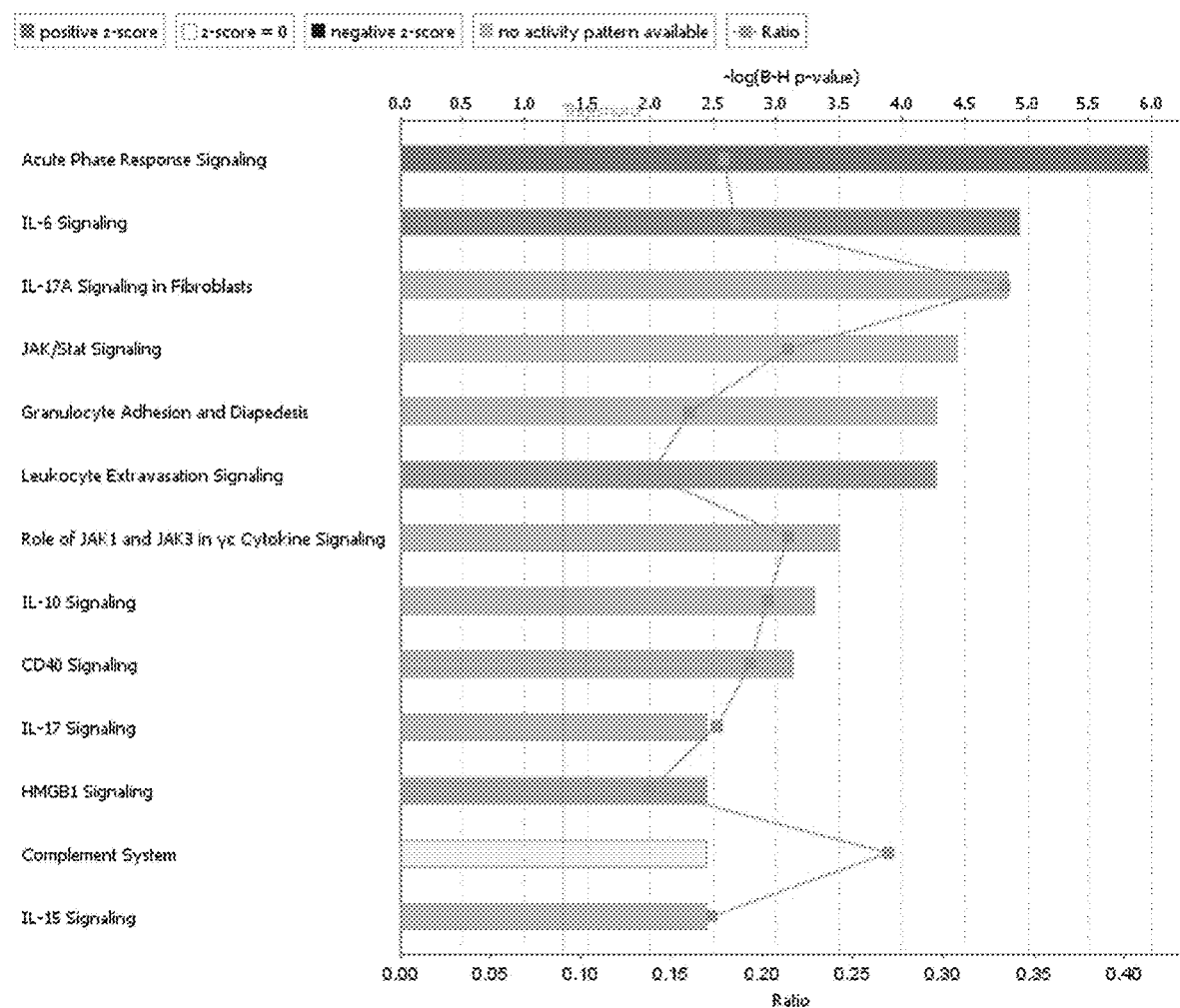
(FIG. 5B) IPA analyses of the top 13 canonical pathways represented by significantly co-expressed mRNA of SAGENT1. Other IPA annotations were the same as FIG. 3b.
Figure 6A:
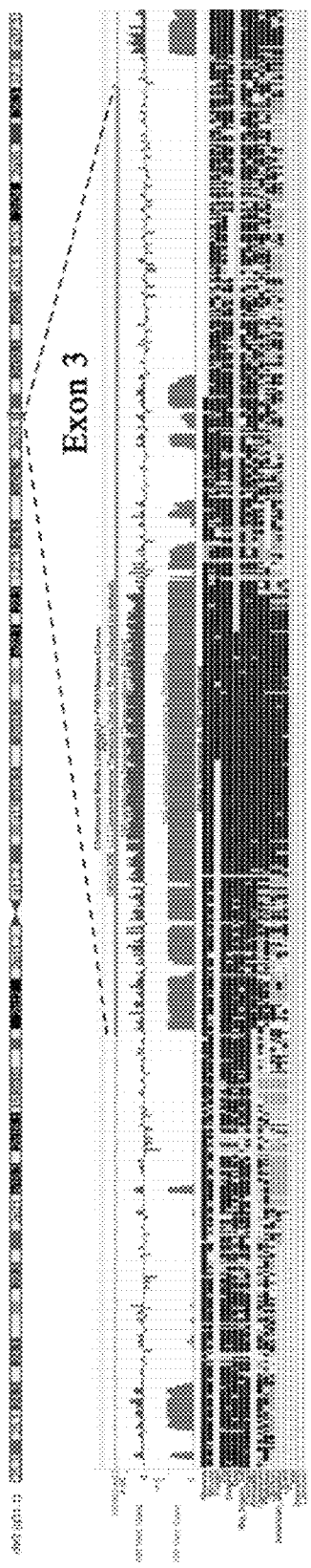
(FIG. 6A) View of UCSC genome browser zoomed in on exon 3 of HOXD-AS2 (HOTAG1) in 2q31.1. Blue vertical bars represented 100 vertebrates' basewise conservation score by PhyloP. Green vertical bars represented 100 vertebrates' conservation by PhastCons scores. Black horizontal bars are Multiz alignments of 100 vertebrates, with names of representative vertebrates listed on the left side of the bars.
Figure 6B:
(FIG. 6B) View of the entire HOXD-AS2 gene, showing conservation scores by PhyloP, PhastCons and Multiz alignments of selected vertebrates across the entire lncRNA.

RP3-449M8.9 is a mono-exonic long intergenic non-coding RNA (lincRNA) located in the gene desert of 14q24.3. FIG. 2 illustrated the Cox proportional hazard survival curves, which showed impairment of survival related to percentile of overexpression of this lincRNA. The other 7 were also novel intergenic lncRNAs with no previous known functions. The Inventors named RP3-449M8.9 as SAGENT1, which stands for Survival Associated Glioblastoma Expressed NonCoding Transcript 1. The other 7 lincRNA were named as SAGENT2 to SAGENT8 (Table 2).

SAGENT1 was differentially expressed in the Inventors' differential expression analyses based on DESeq2 ($\log_2$ fold change=3.90, P=9.52 $E^{-05}$, Q=0.00035), but its expressions did not differ among the TCGA gene expression classes (Spearman p=0.02, P=0.74). Although there are virtually no protein coding genes for >45 Kb centromeric or >4 kb telomeric to SAGENT1, publicly available Chromatin Immunoprecipitation with DNA sequencing (ChIP-Seq) of histone 3 lysine 4 trimethylation (H3K4me3) data (GEO accession 41461) showed the existence of peaks within 3 Kb of SAGENT1 in GBM stem cells (FIG. 2). This suggested there is active transcription of this gene in those GBM cells that retained the capacity of rapid cell division and growth, whereas non-neoplastic neural stem cells harbored no active peaks in the same region surveyed (FIG. 2b). In contrast, there appeared to be less discernible differences in marks of histone 3 lysine 36 trimethylation (H3K36me3) within the gene body of GBM stem cells and neural stem cells. This finding was also consistent with current knowledge that the distribution of H3K36me3 does not differ significantly between tissue and cell types(8). IPA analyses showed that SAGENT1 was associated with 67 significant canonical pathways (Q<0.05), of which 73% of them (49 of 67) were related to innate or acquired cellular immunity in response to inflammatory signals. FIG. 2c illustrated the top 13 pathways.

Among the top 20 differentially expressed lncRNA mentioned above (Table 1), HOTAIRM1 (P=0.039, Q=0.29), AC069363 (P=0.021, Q=0.27), RP11-290F20.3 (P=0.0055, Q=0.17) and RP11-246K15.1 (P=0.048, Q=0.35) were significant in multivariable Cox models but not after false discovery rate adjustment.

Example 9

Discussion

This next-generation RNA-Seq study revealed key novel long non-coding RNA genes that were aberrantly expressed in GBM and had prognostic significance. The HOX gene cluster associated lncRNAs were among the most differentially expressed in GBM. Prior studies have indicated potential importance of anti-sense or intergenic HOX lncRNAs in carcinogenesis. For example, HOTAIR is over-expressed in breast cancer and metastases, and enforced expression of HOTAIR in epithelial cancer cells induced Polycomb Repressive Complex 2 (PRC2) retargeting, altered H3 lysine 27 trimethylation (H3K27me3) and increased in cancer invasiveness. To date, HOTAIR remains the most extensively studied lncRNA in oncogenesis, including one prior study that showed its over-expression in GBM. The Inventors' finding confirmed its important role in gliomagenesis. HOTAIRM1, which was first thought to be involved in granulocytic differentiation, was recently found to be involved in acute myeloid leukemia (AML) and basallike subtype of breast cancer. A study that used 3 pairs of initial and recurrent glioma samples found HOTAIRM1 was upregulated more than 4-folds in the recurrent glioma samples, whereas the Inventors' results suggested that it was already over-expressed at initial diagnoses (492.75 fold changes or $\log_2$ fold changes 6.21). In most of the top differentially expressed lncRNAs, expressions in the normal brain were extremely low in both cerebral cortex and cerebellum. LncRNA expressions are known to vary significantly by neuro-anatomical locations, and the fact that controls from different anatomical regions showed uniformly low expressions strengthened the evidence that these top lncRNAs were aberrantly expressed in tumors.

The novel finding, however, is the prevalence and importance of other HOXD, HOXA and HOXB cluster non-coding transcripts in gliomagenesis. In particular, HOTAG1 (HOXD-AS2) was upregulated 2,275.60 folds ($\log_2$ fold change=7.73) and is at the top of the list of differentially expressed non-coding transcripts. It was most strongly co-expressed with HOXD8, HOXD9 and neighboring HOXD10, raising the possibility of cis regulation of HOTAG1 on local HOXD protein coding genes. The finding of its co-expressions with 771 mRNA genome-wide suggested either it has direct in trans effect on gene expression, or the co-expressed mRNAs were indirectly related to HOTAG1 through HOXD8, HOXD9 and HOXD10. Bioinformatics prediction of its function in the initiation of translation is consistent with known potential functions of lncRNA, although future comprehensive gain or loss of functional experiments will verify the hypothesis that HOTAG1 facilitates protein synthesis through upregulation of EIF2 and EIF4.

The finding of overall low expressions of lncRNA in the Proneural gene expression subgroup is also new and may relate to different genetic lineage of many Proneural GBM. IDH1, IDH2 and ATRX mutations are mostly found within the Proneural group and not in Mesenchymal or Classical subgroups. Moreover, IDH1 or IDH2 mutations are now thought to induce widespread epigenetic changes characterized by G-CIMP via metabolic alterations. Therefore, global reduction in lncRNA expressions within the Proneural group may reflect diffuse chromatin changes caused by metabolic disturbance as well, but future in vitro and in vivo experiments will test this hypothesis.

The 8 most significant lincRNAs appeared to express ubiquitously among mRNA expression classes without differences among Proneural, Neural, Mesenchymal and Classical types. This feature rendered them broadly applicable as survival biomarkers and potential therapeutic targets. Extremely few well validated prognostic biomarkers existed in GBM, although many will agree that MGMT methylation and IDH1 and IDH2 mutations are the most important ones. These results discovered novel markers, but very large series of GBM tissues and annotated clinical databases are needed to ensure the external validity of the findings. Moreover, functional work to elucidate the genomic binding sites of these lincRNAs, and the partnering transcription factors in chromatin modulation will be key to understanding the biological roles of these novel non-coding transcripts as well as the rationale development of therapeutics strategy. In particular, SAGENT1 (RP3-449M8.9), the most prognostic lncRNA for overall survival, appeared to affect host immunity in the Inventors' canonical pathway analyses and can be an attractive target for RNA therapeutics or immune-therapeutics. It may also be of relevance as a predictive biomarker to many of the immunotherapies currently under development in GBM, as host immune functions may affect the efficacy of treatment aiming at harnessing the immune system to attack tumors.

The findings design herein hold promises for much-needed novel biomarkers and therapeutic targets for this devastating disease, and further biological investigation of these significant lncRNAs will deepen the Inventors' understanding of the pathogenesis of this tumor.

This discovery found novel and the most important long non-coding RNAs (lncRNA those RNAs that do not make protein) using the latest agnostic technology: ribo-depleted RNA-Seq. None of the lncRNA the Inventors reported were previously described in glioblastoma multiforme (GBM). The Inventors' findings are important for GBM because currently there are extremely few therapeutic treatment options for this disease, which is very aggressive. The median survival is only about 16 months with the best standard of care. These new lncRNA will serve the purpose of tumor targets for new RNA based biotherapeutics, or as new prognostic biomarkers for this cancer. Novel therapeutics based on the Inventors' findings are important as standard of care treatments have not been able to prolong the lives of these patients for long.

TABLE 1

The top 20 most differentially expressed lncRNA by $\log_2$ fold changes using next gen RNA-Seq. Differential expressions were analyzed with DESeq2.

| LncRNA Name | GENCODE ID | Locus | Mean Counts GBM | Mean Counts Controls | Log2 Fold Changes | P values | FDR Adjusted Q values |
|---|---|---|---|---|---|---|---|
| HOXD-AS2 (HOTAG1) | ENSG00000237380.2 | 2q31.1 | 81.23 | 0.28 | 7.73 | 2.39E−36 | 3.25E−34 |
| HOXA-AS2 (HOTAG2) | ENSG00000253552.3 | 7p15.2 | 206.44 | 1.35 | 6.98 | 7.12E−36 | 9.18E−34 |
| HOXA-AS4 (HOTAG3) | ENSG00000253187.2 | 7p15.2 | 27.79 | 0.16 | 6.78 | 1.71E−15 | 3.15E−14 |
| HOTAIR | ENSG00000228630.1 | 12q13.13 | 114.95 | 0.78 | 6.75 | 1.33E−21 | 4.60E−20 |
| RP11-366L20.3 | ENSG00000256083.1 | 12q14.3 | 29.13 | 0.23 | 6.54 | 2.69E−16 | 5.39E−15 |
| AC069363.1 | ENSG00000224298.2 | 17q12 | 19.33 | 0.11 | 6.48 | 9.30E−11 | 9.69E−10 |
| HOXA-AS3 (HOTAG4) | ENSG00000254369.2 | 7p15.2 | 99.41 | 0.96 | 6.48 | 6.27E−29 | 4.30E−27 |
| HOXB-AS3 (HOTAG5) | ENSG00000233101.6 | 17q21.32 | 26.41 | 0.21 | 6.23 | 1.09E−11 | 1.30E−10 |
| HOTAIRM1 | ENSG00000233429.5 | 7p15.2 | 233.95 | 2.88 | 6.21 | 4.70E−43 | 1.10E−40 |
| RP11-290F20.3 | ENSG00000224397.1 | 20q13.13 | 120.78 | 1.39 | 6.20 | 3.62E−26 | 1.92E−24 |
| DIAPH3-AS1 | ENSG00000227528.1 | 13q21.2 | 7.71 | 0.050 | 6.18 | 2.05E−10 | 2.04E−09 |
| RP11-416O18.1 | ENSG00000242512.4 | 3q26.33 | 300.15 | 4.97 | 5.79 | 2.45E−39 | 4.30E−37 |
| RP11-439H9.1 | ENSG00000235743.1 | 6p22.3 | 27.92 | 0.097 | 5.69 | 9.61E−08 | 6.46E−07 |
| AC074011.2 | ENSG00000230730.1 | 2p23.2 | 25.25 | 0.41 | 5.68 | 1.63E−19 | 4.51E−18 |
| RP11-742B18.1 | ENSG00000249001.1 | 4q22.1 | 97.38 | 1.74 | 5.68 | 3.75E−39 | 6.52E−37 |
| RP11-246K15.1 | ENSG00000253821.1 | 8q12.1 | 21.42 | 0.28 | 5.68 | 9.71E−15 | 1.65E−13 |
| AC005281.1 | ENSG00000226690.2 | 7p21.3 | 37.91 | 0.61 | 5.67 | 9.40E−18 | 2.18E−16 |
| LUCAT1 | ENSG00000248323.1 | 5q14.3 | 392.77 | 7.59 | 5.61 | 1.16E−49 | 4.87E−47 |
| RP11-412H8.2 | ENSG00000258175.1 | 14q12 | 18.15 | 0.29 | 5.58 | 3.95E−15 | 6.99E−14 |
| RP11-536K7.5 | ENSG00000229664.1 | 10p15.1 | 20.84 | 0.30 | 5.56 | 8.65E−13 | 1.18E−11 |

TABLE 2

The 8 lncRNA of prognostic significance in the overall survival of GBM based on multivariable Cox proportional hazard models and adjustments by false discovery rates (FDR). LncRNAs were analyzed with DESeq2.

| LncRNA Name | GENCODE ID | Locus | Hazard Ratio | 95% CI | P value | FDR Q value |
|---|---|---|---|---|---|---|
| RP3-449M8.9 (SAGENT1) | ENSG00000270000 | 14q24.3 | 1.84 | 1.84-2.38 | 2.41E−06 | 0.021 |
| RP11-356N1.2 (SAGENT2) | ENSG00000226822 | 1p13.3 | 1.69 | 1.69-2.15 | 3.02E−05 | 0.037 |
| RP11-329B9.4 (SAGENT3) | ENSG00000272970 | 3q27.1 | 0.47 | 0.47-0.67 | 3.19E−05 | 0.037 |
| CTD-2506J14.1 (SAGENT4) | ENSG00000246084 | 14q32.2 | 1.62 | 1.62-2.03 | 3.40E−05 | 0.037 |
| RP5-1063M23.1 (SAGENT5) | ENSG00000250770 | 12p13.33 | 1.62 | 1.62-2.04 | 3.89E−05 | 0.037 |
| CTD-2532N20.1 (SAGENT6) | ENSG00000272192 | 8q13.1 | 1.64 | 1.64-2.09 | 4.80E−05 | 0.037 |
| RP11-65J3.1 (SAGENT7) | ENSG00000233901 | 9q34.11 | 1.58 | 1.58-1.97 | 4.91E−05 | 0.037 |
| AC112721.2 (SAGENT8) | ENSG00000222032 | 2q37.3 | 1.51 | 1.51-1.86 | 9.56E−05 | 0.048 |

TABLE 3

Demographic and pathological features of GBM cases and control brain tissues.

| ID | TISSUE* | Gender | Age# | Race^ | RIN+ |
|---|---|---|---|---|---|
| RL1 | GBM | M | 63 | C | 7.1 |
| RL2 | GBM | F | 43 | C | 7.0 |
| RL3 | GBM | F | 57 | C | 3.8 |
| RL4 | GBM | M | 58 | C | 1.1 |
| RL5 | GBM | M | 56 | C | 2.8 |
| RL6 | GBM | M | 57 | C | 2.2 |
| RL7 | GBM | F | 43 | C | 7.9 |
| RL15 | CEREBELLUM | F | 55 | C | 7.1 |
| RL16 | CEREBELLUM | F | 56 | C | 7.8 |
| RL17 | CEREBELLUM | F | 57 | C | 5.6 |
| RL18 | CEREBELLUM | M | 55 | C | 6.3 |
| RL19 | CEREBELLUM | M | 55 | C | 6.0 |
| RL20 | CEREBELLUM | M | 57 | C | 6.3 |
| RL21 | CORTEX | F | 60 | C | 7.7 |
| RL22 | CORTEX | M | 60 | C | 8.1 |
| RL23 | CORTEX | F | 60 | C | 7.1 |
| RL24 | CORTEX | M | 56 | C | 6.0 |
| RL25 | CORTEX | F | 56 | C | 7.4 |
| RL26 | CORTEX | M | 56 | C | 6.1 |
| RL27 | GBM | M | 81 | C | 6.9 |
| RL28 | GBM | F | 59 | C | 8.0 |
| RL29 | GBM | F | 57 | C | 8.3 |
| RL30 | GBM | M | 39 | C | 7.5 |
| RL31 | GBM | F | 50 | C | 7.8 |
| RL32 | GBM | M | 49 | C | 7.3 |
| RL33 | GBM | F | 76 | A | 7.0 |
| RL34 | GBM | M | 64 | C | 2.3 |
| RL35 | GBM | M | 48 | C | 6.5 |
| RL36 | GBM | M | 54 | A | 6.0 |
| RL37 | GBM | M | 61 | C | 7.4 |
| RL38 | GBM | M | 76 | C | 7.5 |
| RL39 | GBM | M | 66 | C | 8.1 |
| RL40 | CORTEX | M | 64 | C | 7.3 |
| RL41 | CORTEX | M | 62 | C | 4.2 |
| RL42 | CORTEX | M | 56 | A | 7.4 |
| RL43 | CORTEX | F | 82 | C | 6.9 |
| RL44 | CORTEX | F | 61 | C | 6.8 |
| RL45 | CORTEX | M | 55 | C | 5.4 |
| RL46 | CORTEX | F | 63 | C | 6.8 |

*GBM = glioblastoma multiforme; cortex = cortical brain controls; cerebellum: cerebellar controls.
Age at diagnosis for tumors and age at the time of autopsy for controls.
^C = Caucasian; A = Asian
+RIN = RNA integrity number

TABLE 4

RT-PCR Primers

| Gene/primer (forward) | Sequence (5'-3') | Gene/primer (reverse) | Sequence (5'-3') |
|---|---|---|---|
| HOX-AS2-f | TCCCCCTGAAAGTAAATGTCCTT [SEQ ID NO: 1] | HOX-AS2-r | CCCGTGTTTGCTGAATCCTT [SEQ ID NO: 2] |
| RP11-745C15.2-f | TTTTGGAGCACAAGCCTTCTG [SEQ ID NO: 3] | RP11-745C15.2-r | CACGACGATGCCATGGAA [SEQ ID NO: 4] |
| H19-f | TCCCAGAACCCACAACATGA [SEQ ID NO: 5] | H19-r | GGGTTTTGTGTCCGGATTCA [SEQ ID NO: 6] |
| RP11-545H22.1-f | CCTCTGGACATGCCATGAAA [SEQ ID NO: 7] | RP11-545H22.1-r | TCCTATCTCTCCTTGGTCTTCAAAA [SEQ ID NO: 8] |
| LUCAT1-f | CCAACGCTTGCCAAATCCT [SEQ ID NO: 9] | LUCAT1-r | ACGGTAGTGACAGCATCAAAACTC [SEQ ID NO: 10] |
| RP11-731F5.2-f | GGCCGAGCTGTGATTTCCTA [SEQ ID NO: 11] | RP11-731F5.2-r | GGGTCTCAGCCCTTCCTGTT [SEQ ID NO: 12] |
| RP11-439H9.1-f | TTTGTACCACCCTAACCTTTGCTT [SEQ ID NO: 13] | RP11-439H9.1-r | CTGCTTAACATGCTGCAACCA [SEQ ID NO: 14] |

TABLE 4-continued

RT-PCR Primers

| Gene/primer (forward) | Sequence (5'-3') | Gene/primer (reverse) | Sequence (5'-3') |
|---|---|---|---|
| RP11-84A19.3-f | GGACCCTGCTGTGTCTGGAA [SEQ ID NO: 15] | RP11-84A19.3-r | GCAGGCCTTTGGGCTCTT [SEQ ID NO: 16] |
| RP1-170O19.23-f | GCACCAGGAAAGAGGACAATTC [SEQ ID NO: 17] | RP1-170O19.23-r | CGGTGGCTCCCAGAAGCT [SEQ ID NO: 18] |
| HOXA-AS3-f | GCTGCATCCAAGGGTAAACC [SEQ ID NO: 19] | HOXA-AS3-r | GCAAAGCACTCCATGACGAA [SEQ ID NO: 20] |
| RP1-140K8.5-f | ACAGGGTCCCCCGACAGA [SEQ ID NO: 21] | RP1-140K8.5-r | AGCACGAACTGTCCCCAGAT [SEQ ID NO: 22] |
| AC096579.7-f | TTCGGCCAAGGGACCAA [SEQ ID NO: 23] | AC096579.7-r | GATGGCGGGAAGATGAAGAC [SEQ ID NO: 24] |
| HOXA-A54-f | TGGGAGGCTCAGGATGGA [SEQ ID NO: 25] | HOXA-A54-r | GTGGTAGGAATTCTGGGCTTTG [SEQ ID NO: 26] |
| RP11-1151B14.4-f | TGGCTTTCTCTGCTATCAGCAA [SEQ ID NO: 27] | RP11-1151B14.4-r | GAATTGGCCCCCTCTGAAAT [SEQ ID NO: 28] |
| HOTAIRM1-f | GGCTTCCGCAGTGATGGA [SEQ ID NO: 29] | HOTAIRM1-r | CGACTGCGCGTCACCTAGA [SEQ ID NO: 30] |
| GNAS-AS1-f | CCCAGGATGGATAAGGAGTTGA [SEQ ID NO: 31] | GNAS-AS1-r | CTGGTAGCCAGTCACTTCCACTT [SEQ ID NO: 32] |
| HOXA-AS2-f | CGGGCCCTTTGCGTCTA [SEQ ID NO: 33] | HOXA-AS2-r | AAGAGGTTACCTGGGTCTGAGTGA [SEQ ID NO: 34] |
| HOXB-AS3-f | TATAGAAACCAGGACGTCCCTTAGC [SEQ ID NO: 35] | HOXB-AS3-r | CGCTGGTGCGGATATCG [SEQ ID NO: 36] |
| RP11-366L20.3-f | GGTTACATGGGAGGGTTTGGT [SEQ ID NO: 37] | RP11-366L20.3-r | AGAAGGTGCAGAGCAGCAAGTT [SEQ ID NO: 38] |
| RP1-58B11.1-f | GCCAGAAGACATGTAAACAGTGACA [SEQ ID NO: 39] | RP1-58B11.1-r | AGGAGTGGAGAAGCATTACAAGATG [SEQ ID NO: 40] |
| SAA2-SAA4-f | TGACGGCCTGCCTAAGAAAT [SEQ ID NO: 41] | SAA2-SAA4-r | TGTGGCTCACAGCCCAGTT [SEQ ID NO: 42] |
| HOTAIR-f | CCTAGCCTTTGGAAGCTCTTGA [SEQ ID NO: 43] | HOTAIR-r | TGTCTTGGAGAGGCGTGTAACA [SEQ ID NO: 44] |
| RP11-79H23.3-f | AGAGAGAAGGCATACTGTTGATGGT [SEQ ID NO: 45] | RP11-79H23.3-r | CAGCACGTGACTTTTGTTGTTTT [SEQ ID NO: 46] |
| RP11-246K15.1-f | GAGGCAAACATGTTCCAAAGAAG [SEQ ID NO: 47] | RP11-246K15.1-r | GCATTGTATCTTTTCGGTGAATTTT [SEQ ID NO: 48] |
| AC010729.1-f | TCAGGGACAGGCTTGAAGATTC [SEQ ID NO: 49] | AC010729.1-r | TCCTGCCGAGGCTGACA [SEQ ID NO: 50] |
| hACTINalpha-f | CAGGACCGTGTGGAGCAGATTG [SEQ ID NO: 51] | hACTINalpha-r | CAGATTGTCCCACTGGTCACAG [SEQ ID NO: 52] |
| hGAPDH-f | TGCCCTCAACGACCACTTTG [SEQ ID NO: 53] | hGAPDH-r | CTCTTCCTCTTGTGCTCTTGCTG [SEQ ID NO: 54] |
| hRPLP0-f | CGCTATCCGCGGTTTCTGATTG [SEQ ID NO: 55] | hRPLP0-r | AAAGACGATGTCACTTCCACGAG [SEQ ID NO: 56] |

TABLE 5

Demographics, clinical and molecular characteristics of the 153 TCGA GBM cases.

| Characteristics | N (Total = 153) |
|---|---|
| Age (Median (IQR)) | 60 (52.0-69.5) |
| Year of Diagnosis (range) | 2005-2009 |
| Female (%) | 54 (35.29) |
| Concomitant Temozolomide | 103 (67.32) |

TABLE 5-continued

Demographics, clinical and molecular characteristics of the 153 TCGA GBM cases.

| Characteristics | N (Total = 153) |
|---|---|
| with Cranial Radiotherapy (%) | |
| Bevacizumab at tumor recurrence (%) | 28 (18.30) |
| MGMT Methylation (%) | 60 (39.22) |
| GCIMP (%) | 11 (7.19) |
| KPS (Median (IQR)) | 80 (60-80)* |
| Participating Center | |
| Center 6 | 57 (37.25) |
| Center 28 | 15 (9.80) |
| Center 27 | 12 (7.84) |
| Center 14 | 11 (7.19) |
| Center 12 | 10 (6.54) |
| Center 32 | 10 (6.54) |
| Center 2, 8, 15, 16, 19, 26, 41 and 76 | 38 (24.84) |
| TCGA mRNA Expression Clusters | |
| Classical | 39 (25.49) |
| Proneural-G-CIMP | 11 (7.14) |
| Proneural-non G-CIMP | 29 (18.95) |
| Mesenchymal | 48 (31.37) |
| Neural | 26 (16.99) |

*41 cases missing KPS data.

TABLE 6

Results of RT-PCR validation of lncRNA expressions.

| Gene | Mean Ct* GBM | Mean Ct Control | Mean dCt^ GBM | Mean dCt Control | ddCt (GBM dCt-Control dCt) | Fold Change# (GBM/Control) | P values |
|---|---|---|---|---|---|---|---|
| HOX-AS2 | 28.5636 | 37.4359 | 4.4761 | 13.3589 | −8.8829 | 472.076 | <0.000001 |
| RP11-745C15.2 | 26.7537 | 30.1075 | 2.6661 | 6.0306 | −3.3644 | 10.299 | <0.000001 |
| H19 | 24.5356 | 27.7213 | 0.4480 | 3.6444 | −3.1963 | 9.166 | <0.000001 |
| RP11-545H22.1 | 28.1263 | 30.6994 | 4.0387 | 6.6224 | −2.5837 | 5.995 | <0.00007 |
| LUCAT1 | 27.5448 | 31.2862 | 3.4572 | 7.2093 | −3.7520 | 13.473 | <0.000001 |
| RP11-731F5.2 | 27.1399 | 29.8368 | 3.0523 | 5.7598 | −2.7075 | 6.532 | <0.00002 |
| RP11-439H9.1 | 40.0000 | 40.0000 | 15.9124 | 15.9230 | −0.0106 | 1.007 | 0.97040 |
| RP11-84A19.3 | 24.4943 | 30.3240 | 0.4068 | 6.2470 | −5.8403 | 57.292 | <0.000001 |
| RP1-170O19.23 | 27.6634 | 31.7736 | 3.5758 | 7.6966 | −4.1208 | 17.398 | <0.000001 |
| HOXA-AS3 | 26.1780 | 31.9942 | 2.0904 | 7.9172 | −5.8269 | 56.762 | <0.000001 |
| RP1-140K8.5 | 26.2885 | 30.4380 | 2.2010 | 6.3610 | −4.1601 | 17.878 | <0.000001 |
| AC096579.7 | 27.1357 | 30.1671 | 3.0481 | 6.0901 | −3.0420 | 8.236 | <0.00002 |
| HOXA-AS4 | 27.1853 | 31.5783 | 3.0977 | 7.5013 | −4.4036 | 21.165 | <0.000001 |
| RP11-1151B14.4 | 26.5662 | 31.2743 | 2.4786 | 7.1974 | −4.7188 | 26.333 | <0.000001 |
| HOTAIRVI1 | 26.0630 | 30.8120 | 1.9754 | 6.7350 | −4.7597 | 27.089 | <0.000001 |
| GNAS-AS1 | 31.4397 | 33.9164 | 7.3521 | 9.8394 | −2.4873 | 5.607 | <0.000001 |
| HOXA-AS2 | 27.5969 | 32.0381 | 3.5093 | 7.9611 | −4.4518 | 21.885 | <0.000001 |
| HOXB-AS3 | 28.5611 | 31.5762 | 4.4735 | 7.4993 | −3.0258 | 8.144 | <0.000001 |
| RP11-366L20.3 | 27.9022 | 31.3823 | 3.8146 | 7.3053 | −3.4908 | 11.242 | <0.000001 |
| RP1-58B11.1 | 28.0902 | 31.2243 | 4.0026 | 7.1473 | −3.1447 | 8.844 | <0.000001 |
| SAA2-SAA4 | 28.7094 | 30.2530 | 4.6218 | 6.1760 | −1.5543 | 2.937 | <0.00172 |
| HOTAIR | 27.6961 | 32.1558 | 3.6085 | 8.0788 | −4.4703 | 22.166 | <0.000001 |
| RP11-79H23.3 | 26.9652 | 30.6346 | 2.8776 | 6.5577 | −3.6801 | 12.818 | <0.000001 |
| RP11-246K15.1 | 27.4499 | 31.1799 | 3.3624 | 7.1030 | −3.7406 | 13.367 | <0.000001 |
| AC010729.1 | 26.0316 | 29.4300 | 1.9440 | 5.3531 | −3.4090 | 10.622 | <0.000001 |
| Reference Genes | | | | | | | |
| αACTIN | 22.0915 | 22.2926 | −1.9961 | −1.7844 | −0.2118 | 1.158 | 0.11487 |
| GAPDH | 16.9785 | 16.9332 | −7.1091 | −7.1438 | 0.0347 | −1.024 | 0.72185 |
| RPLP0 | 33.1928 | 33.0051 | 9.1052 | 8.9281 | 0.1771 | −1.131 | 0.34104 |

*Ct = counts
^dCt = (Ct (gene of interest)-Ct (reference genes))
Fold changes = $2^{(-ddCt)}$

TABLE 7

The 8 lncRNA of prognostic significance in the overall survival of GBM based on multivariable Cox proportional hazard models and P values adjusted by false discovery rates (FDR). Transcripts were assembled with Cufflink 2.

| LncRNA Name | GENCODE ID | Locus | Hazard Ratio | 95% CI | P value | FDR Q value |
|---|---|---|---|---|---|---|
| RP3-449M8.9 (SARGENT1) | ENSG00000270000 | 14q24.3 | 8.73 | 3.88-19.68 | 1.71E−07 | 0.0011 |
| RP11-356N1.2 (SARGENT2) | ENSG00000226822 | 1p13.3 | 6.43 | 2.60-15.95 | 5.85E−05 | 0.026 |
| RP11-329B9.4 (SARGENT3) | ENSG00000272970 | 3q27.1 | 0.36 | 0.22-0.59 | 6.22E−05 | 0.026 |
| CTD-2506J14.1 (SARGENT4) | ENSG00000246084 | 14q32.2 | 26.41 | 4.60-151.56 | 0.00024 | 0.050 |
| RP5-1063M23.1 (SARGENT5) | ENSG00000250770 | 12p13.33 | 350.44 | 22.24-5522.28 | 3.12E−05 | 0.026 |
| CTD-2532N20.1 (SARGENT6) | ENSG00000272192 | 8q13.1 | 2.62 | 1.65-4.16 | 4.39E−05 | 0.026 |
| RP11-65J3.1 (SARGENT7) | ENSG00000233901 | 9q34.11 | 1.66 | 1.30-2.11 | 3.74E−05 | 0.026 |
| AC112721.2 (SARGENT8) | ENSG00000222032 | 2q37.3 | 437.62 | 27.83-6882.19 | 1.52E−05 | 0.026 |

TABLE 8

The differences of $R^2$ between training and validation sets of the 8 prognostic lncRNAs, the standard errors and 95% confidence intervals of the $R^2$ differences

| lncRNA | $R^2$ Training Set | $R^2$ Validation Set | SE Training Set | SE Validation Set | Difference of $R^2$ | SE Difference of $R^2$ | Absolute Value of Difference | Lower 95% CI of Difference | Upper 95% CI of Difference |
|---|---|---|---|---|---|---|---|---|---|
| RP3-449M8.9 | 0.270377 | 0.204132 | 0.089062 | 0.089575 | −0.066245 | 0.12631595 | 0.066245 | −0.060071 | 0.19256094 |
| AC112721.2 | 0.286918 | 0.17561 | 0.088748 | 0.07536 | −0.111308 | 0.11642739 | 0.111308 | −0.0051194 | 0.2277354 |
| CTD-2532N20.1 | 0.269147 | 0.221105 | 0.129404 | 0.072469 | −0.048042 | 0.14831437 | 0.048042 | −0.1002724 | 0.19635637 |
| RP11-329B9.4 | 0.204669 | 0.239197 | 0.129591 | 0.118786 | 0.034528 | 0.17579517 | 0.034528 | −0.1412672 | 0.21032317 |
| RP11-65J3.1 | 0.231625 | 0.230938 | 0.068458 | 0.086054 | −0.000687 | 0.10996267 | 0.000687 | −0.1092757 | 0.11064968 |
| CTD-2506J14.1 | 0.226301 | 0.230537 | 0.131598 | 0.084324 | 0.004236 | 0.15629642 | 0.004236 | −0.1520604 | 0.16053241 |
| RP11-356N1.2 | 0.242918 | 0.114693 | 0.091275 | 0.109206 | −0.128225 | 0.14232735 | 0.128225 | −0.0141024 | 0.27055234 |
| RP5-1063M23.1 | 0.258233 | 0.16616 | 0.079211 | 0.074014 | −0.092073 | 0.10840874 | 0.092073 | −0.0163357 | 0.20048174 |

TABLE 9

Additional Validation using TCGA with 4 normals

| LncRNA Name | GENCODE ID | Base Mean | log2Fold Change | SE | Stat | P | FDRQ | P (Adj for Proneural) | FDRQ (Adj for Proneural) | Original P |
|---|---|---|---|---|---|---|---|---|---|---|
| HOTAIRM1 | ENSG00000233429.5 | 604.857721 | 5.79283756 | 0.67704728 | 8.56E+00 | 1.17E−17 | 7.13E−16 | 1.79E−17 | 9.24E−16 | 1.10E−40 |
| HOXA-AS2 (HOTAG2) | ENSG00000253552.3 | 271.78346 | 8.77369254 | 1.04381116 | 8.41E+00 | 4.26E−17 | 2.41E−15 | 9.78E−17 | 4.66E−15 | 9.18E−34 |
| HOXD-AS2 (HOTAG1) | ENSG00000237380.2 | 97.0913749 | 8.01103559 | 1.07540072 | 7.45E+00 | 9.38E−14 | 3.26E−12 | 4.84E−13 | 1.34E−11 | 3.25E−34 |
| HOTAIR | ENSG00000228630.1 | 279.298257 | 7.33881094 | 1.0612804 | 6.92E+00 | 4.68E−12 | 1.25E−10 | 3.60E−12 | 8.64E−11 | 4.60E−20 |
| RP11-742B18.1 | ENSG00000249001.1 | 79.0826365 | 7.27163869 | 1.11370365 | 6.53E+00 | 6.61E−11 | 1.44E−09 | 1.56E−11 | 3.33E−10 | 6.52E−37 |
| HOXA-AS3 (HOTAG4) | ENSG00000254369.2 | 54.6441658 | 7.26015874 | 1.11231136 | 6.53E+00 | 6.71E−11 | 1.46E−09 | 1.29E−10 | 2.32E−09 | 4.30E−27 |
| RP11-416O18.1 | ENSG00000242512.4 | 134.066683 | 4.63588513 | 0.81737584 | 5.67E+00 | 1.41E−08 | 1.93E−07 | 2.24E−09 | 3.13E−08 | 4.30E−37 |
| RP11-290F20.3 | ENSG00000224397.1 | 209.572607 | 2.97735798 | 0.71935776 | 4.14E+00 | 3.49E−05 | 0.0002135 | 5.24E−06 | 3.53E−05 | 1.92E−24 |
| AC074011.2 | ENSG00000230730.1 | 13.0249232 | 2.62795858 | 0.69735356 | 3.76847374 | 0.00016425 | 0.00083476 | 3.77E−05 | 2.06E−04 | 4.51E−18 |
| AC005281.1 | ENSG00000226690.2 | 17.2272927 | 4.0578831 | 1.15399043 | 3.51639232 | 0.00043745 | 0.00197788 | 1.28E−04 | 6.15E−04 | 2.18E−16 |
| RP11-246K15.1 | ENSG00000253821.1 | 10.25214 | 3.64679209 | 1.12477648 | 3.24223714 | 0.00118595 | 0.00469097 | 6.33E−04 | 2.54E−03 | 1.65E−13 |

TABLE 9-continued

Additional Validation using TCGA with 4 normals

| LncRNA Name | GENCODE ID | Base Mean | log2Fold Change | SE | Stat | P | FDRQ | P (Adj for Pro-neural) | FDRQ (Adj for Pro-neural) | Orig-inalP |
|---|---|---|---|---|---|---|---|---|---|---|
| HOXB-AS3 (HOTAG5) | ENSG00000233101.6 | 15.2468518 | 4.18638223 | 1.30925074 | 3.19754046 | 0.00138605 | 0.00536272 | 8.18E-04 | 3.18E-03 | 1.30E-10 |
| RP11-536K7.5 | ENSG00000229664.1 | 3.37257995 | 3.08549975 | 1.13944916 | 2.70788717 | 0.0067713 | 0.02082861 | 4.33E-03 | 1.34E-02 | 1.18E-11 |
| RP11-439H9.1 | ENSG00000235743.1 | 9.37865447 | 3.91168004 | 1.32981706 | 2.94151741 | 0.00326608 | 0.01122585 | 5.27E-03 | 1.59E-02 | 6.46E-07 |
| AC069363.1 | ENSG00000224298.2 | 2.08252453 | 3.43256874 | 1.36492282 | 2.51484458 | 0.01190849 | 0.03344871 | 7.59E-03 | 2.17E-02 | 9.69E-10 |
| HOXA-AS4 (HOTAG3) | ENSG00000253187.2 | 10.6674119 | 3.12815304 | 1.26184273 | 2.4790356 | 0.01317382 | 0.03633194 | 1.34E-02 | 3.52E-02 | 3.15E-14 |
| RP11-412H8.2 | ENSG00000258175.1 | 1.22710487 | 2.91974187 | 1.40637153 | 2.07608147 | 0.03788642 | 0.08653141 | 3.36E-02 | 7.56E-02 | 6.99E-14 |
| RP11-366L20.3 | ENSG00000256083.1 | 1.81617264 | 2.20169536 | 1.25027867 | 1.7609637 | 0.07824455 | 0.15363824 | 6.85E-02 | 1.35E-01 | 5.39E-15 |
| LUCAT1 | ENSG00000248323.1 | 45.1301101 | 0.58713069 | 0.75881829 | 0.77374346 | 0.43908251 | 0.56987414 | 4.04E-01 | 5.30E-01 | 4.87E-47 |
| DIAPH3-AS1 | ENSG00000227528.1 | 0.08212963 | 0.3302192 | 1.35576203 | 0.24356723 | 0.80756601 | NA | 8.40E-01 | NA | 2.04E-09 |

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are sources of long non-coding RNAs (lncRNA), methods of detecting, isolating, synthesizing or otherwise manipulating lncRNAs, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of prognosing susceptibility to a brain tumor comprising:
   providing a sample from a subject; and
   detecting one or more long non-coding RNAs (lncRNAs) in the sample, wherein the detected level of the one or more lncRNAs in the same from the subject compared to a reference level of the one or more lncRNAs prognoses susceptibility to a brain tumor, wherein detecting one or more long non-coding RNAs (lncRNAs) comprises ribo-depleted RNA sequencing.

2. The method of claim 1, wherein the brain tumor comprises glioblastoma multiforme (GBM).

3. The method of claim 1, wherein the brain tumor comprises astrocytoma.

4. The method of claim 1, wherein the one or more lncRNAs comprises HOXD-AS2 (HOTAG1), HOXA-AS2 (HOTAG2), HOXA-AS4 (HOTAG3), HOTAIR, RP11-

366L20.3, AC069363.1, HOXA-AS3 (HOTAG4), HOXB-AS3 (HOTAG5), HOTAIRM1, RP11-290F20.3, DIAPH3-AS1, RP11-416018.1, RP11-439H9.1, AC074011.2, RP11-742B18.1, RP11-246K15.1, AC005281.1, LUCAT1, RP11-412H8.2, and/or RP11-536K7.5.

5. The method of claim 1, wherein detecting one or more long non-coding RNAs (lncRNAs) comprises quantitative real-time PCR (qRT-PCR).

6. A method of determining the presence or absence of a brain tumor comprising:
providing a sample from a subject; and
detecting one or more long non-coding RNAs (lncRNAs) in the sample, wherein the detected level of the one or more lncRNAs in the same from the subject compared to a reference level of the one or more lncRNAs determines the presence or absence of a brain tumor in the subject, wherein detecting one or more long non-coding RNAs (lncRNAs) comprises ribo-depleted RNA sequencing.

7. The method of claim 6, wherein the brain tumor comprises glioblastoma multiforme (GBM).

8. The method of claim 6, wherein the brain tumor comprises astrocytoma.

9. The method of claim 6, wherein the one or more lncRNAs comprises HOXD-AS2 (HOTAG1), HOXA-AS2 (HOTAG2), HOXA-AS4 (HOTAG3), HOTAIR, RP11-366L20.3, AC069363.1, HOXA-AS3 (HOTAG4), HOXB-AS3 (HOTAG5), HOTAIRM1, RP11-290F20.3, DIAPH3-AS1, RP11-416018.1, RP11-439H9.1, AC074011.2, RP11-742B18.1, RP11-246K15.1, AC005281.1, LUCAT1, RP11-412H8.2, and/or RP11-536K7.5.

10. The method of claim 6, wherein detecting one or more long non-coding RNAs (lncRNAs) comprises quantitative real-time PCR (qRT-PCR).

* * * * *